United States Patent
Vyas et al.

(10) Patent No.: US 12,290,258 B2
(45) Date of Patent: May 6, 2025

(54) STAPLER APPARATUS AND METHODS FOR USE

(71) Applicants: Dinesh Vyas, Elk Grove, CA (US);
Anoushka Vyas, Elk Grove, CA (US);
Stephane M. Gobron, San Marino, CA (US)

(72) Inventors: Dinesh Vyas, Elk Grove, CA (US);
Anoushka Vyas, Elk Grove, CA (US);
Stephane M. Gobron, San Marino, CA (US)

( * ) Notice: Subject to any disclaimer, the term of this patent is extended or adjusted under 35 U.S.C. 154(b) by 0 days.

(21) Appl. No.: 17/384,774

(22) Filed: Jul. 25, 2021

(65) Prior Publication Data
US 2022/0008068 A1    Jan. 13, 2022

Related U.S. Application Data

(63) Continuation-in-part of application No. 16/874,618, filed on May 14, 2020.
(Continued)

(51) Int. Cl.
*A61B 17/068* (2006.01)
*A61B 1/00* (2006.01)
(Continued)

(52) U.S. Cl.
CPC ........ *A61B 17/0686* (2013.01); *A61B 1/0017* (2013.01); *A61B 1/018* (2013.01);
(Continued)

(58) Field of Classification Search
CPC ... A61B 1/00052; A61B 1/0017; A61B 1/018; A61B 1/042; A61B 1/051; A61B 17/0686; A61B 17/072; A61B 17/07207; A61B 90/37; A61B 2017/00115; A61B 2017/00823; A61B 2017/07228;
(Continued)

(56) References Cited

U.S. PATENT DOCUMENTS

| | | |
|---|---|---|
| 3,612,107 A | 10/1971 | Grise |
| 3,940,844 A | 3/1976 | Colby |

(Continued)

FOREIGN PATENT DOCUMENTS

| | | |
|---|---|---|
| EP | 1157666 A1 | 11/2001 |
| EP | 3409217 A1 | 12/2018 |
| WO | 2013134411 A1 | 9/2013 |

*Primary Examiner* — Robert F Long
*Assistant Examiner* — Eduardo R Ferrero
(74) *Attorney, Agent, or Firm* — William A. English; Vista IP Law Group LLP

(57) ABSTRACT

Apparatus and methods are provided for performing a medical procedure, such as a laparoscopic appendectomy or tubal ligation, using a stapler apparatus including a handle portion including a shaft include proximal and distal ends, an end effector attached to the distal end of the shaft of the handle carrying one or more staples, and an imaging sleeve carried on the shaft. For example, the end effector may include first and second jaws movable relative to one another between open and closed positions, the first jaw carrying a cartridge which includes the one or more staples. The end effector is introduced into a patient's body, tissue is positioned/locked between the jaws, and a plurality of staples are deployed into the tissue.

25 Claims, 23 Drawing Sheets

Related U.S. Application Data

(60) Provisional application No. 62/947,903, filed on Dec. 13, 2019.

(51) Int. Cl.

| | |
|---|---|
| *A61B 1/018* | (2006.01) |
| *A61B 1/04* | (2006.01) |
| *A61B 17/072* | (2006.01) |
| *A61B 1/005* | (2006.01) |
| *A61B 17/00* | (2006.01) |
| *A61B 90/00* | (2016.01) |

(52) U.S. Cl.
CPC ............ *A61B 1/042* (2013.01); *A61B 17/072* (2013.01); *A61B 1/00052* (2013.01); *A61B 1/0051* (2013.01); *A61B 2017/00115* (2013.01); *A61B 2017/00823* (2013.01); *A61B 17/07207* (2013.01); *A61B 2017/07228* (2013.01); *A61B 2017/07235* (2013.01); *A61B 2017/07242* (2013.01); *A61B 2017/07257* (2013.01); *A61B 2017/07271* (2013.01); *A61B 2017/07278* (2013.01); *A61B 90/37* (2016.02)

(58) Field of Classification Search
CPC ........... A61B 2017/07235; A61B 2017/07242; A61B 2017/07257; A61B 2017/07271; A61B 2090/372; A61B 2090/3983
See application file for complete search history.

(56) References Cited

U.S. PATENT DOCUMENTS

| | | | |
|---|---|---|---|
| 4,423,787 A | 1/1984 | Steinberg | |
| 4,487,394 A | 12/1984 | Rothfuss | |
| 4,526,174 A | 7/1985 | Froehlich | |
| 4,655,222 A | 4/1987 | Florez | |
| 4,676,245 A | 6/1987 | Fukuda | |
| 4,706,864 A | 11/1987 | Jacobsen | |
| 4,773,420 A | 9/1988 | Green | |
| 4,787,387 A | 11/1988 | Burbank, III | |
| 4,802,478 A | 2/1989 | Powell | |
| 4,848,637 A | 7/1989 | Pruitt | |
| 4,887,601 A | 12/1989 | Richards | |
| 4,919,021 A | 4/1990 | Franks | |
| 4,924,864 A | 5/1990 | Danzig | |
| 4,998,981 A | 3/1991 | Miyanaga | |
| 5,095,590 A | 3/1992 | Schick | |
| 5,163,598 A | 11/1992 | Peters | |
| 5,166,787 A | 11/1992 | Irion | |
| 5,192,288 A | 3/1993 | Thompson | |
| 5,250,058 A | 10/1993 | Miller | |
| 5,258,016 A | 11/1993 | DiPoto | |
| 5,282,829 A | 2/1994 | Hermes | |
| 5,389,098 A | 2/1995 | Tsuruta | |
| 5,395,030 A | 3/1995 | Kuramoto | |
| 5,403,326 A | 4/1995 | Harrison | |
| 5,423,857 A | 6/1995 | Rosenman | |
| 5,489,058 A | 2/1996 | Plyley | |
| 5,497,933 A | 3/1996 | DeFonzo | |
| 5,535,935 A | 7/1996 | Vidal | |
| 5,573,543 A | 11/1996 | Akopov | |
| 5,624,452 A | 4/1997 | Yates | |
| 5,643,291 A | 7/1997 | Pier | |
| 5,658,312 A | 8/1997 | Green | |
| 5,709,680 A | 1/1998 | Yates et al. | |
| 5,755,732 A | 5/1998 | Green | |
| 5,810,846 A | 9/1998 | Vimich | |
| 5,893,855 A | 4/1999 | Jacobs | |
| 5,893,863 A | 4/1999 | Yoon | |
| 5,928,137 A | 7/1999 | Green | |
| 5,972,002 A | 10/1999 | Bark | |
| 5,984,692 A | 11/1999 | Kumagai | |
| 6,003,517 A | 12/1999 | Sheffield et al. | |
| 6,059,787 A | 5/2000 | Allen | |
| 6,083,241 A | 7/2000 | Longo | |
| 6,165,204 A | 12/2000 | Levinson | |
| 6,178,346 B1 * | 1/2001 | Amundson | A61B 1/00165 600/473 |
| 6,211,904 B1 * | 4/2001 | Adair | H01L 25/167 257/E25.032 |
| 6,221,007 B1 | 4/2001 | Green | |
| 6,254,615 B1 | 7/2001 | Bolduc | |
| 6,277,064 B1 * | 8/2001 | Yoon | A61B 1/00177 600/173 |
| 6,309,345 B1 | 10/2001 | Stelzer | |
| 6,387,043 B1 * | 5/2002 | Yoon | A61B 1/05 600/129 |
| 6,419,626 B1 * | 7/2002 | Yoon | A61B 1/00052 600/117 |
| 6,419,682 B1 | 7/2002 | Appleby | |
| 6,471,637 B1 * | 10/2002 | Green | A61B 1/00045 600/137 |
| 6,530,933 B1 | 3/2003 | Yeung | |
| 6,648,816 B2 * | 11/2003 | Irion | A61B 17/00234 600/173 |
| 6,671,581 B2 * | 12/2003 | Niemeyer | A61B 34/77 600/109 |
| 6,718,196 B1 | 4/2004 | Mah | |
| 6,739,374 B1 | 5/2004 | Mouzakis | |
| 6,981,983 B1 | 1/2006 | Rosenblatt | |
| 7,048,255 B2 | 5/2006 | Buch | |
| 7,213,736 B2 | 5/2007 | Wales | |
| 7,267,682 B1 | 9/2007 | Bender | |
| 7,381,183 B2 * | 6/2008 | Hale | A61B 1/0005 600/117 |
| 7,431,730 B2 | 10/2008 | Viola | |
| 7,438,209 B1 | 10/2008 | Hess | |
| 7,621,925 B2 | 11/2009 | Saadat | |
| 7,699,860 B2 | 4/2010 | Huitema | |
| 7,744,613 B2 | 6/2010 | Ewers | |
| 7,776,057 B2 | 8/2010 | Aufer | |
| 7,780,663 B2 | 8/2010 | Yates et al. | |
| 7,871,416 B2 | 1/2011 | Phillips | |
| 7,875,063 B1 | 1/2011 | Sander | |
| 7,918,873 B2 | 4/2011 | Cummins | |
| 7,946,981 B1 | 5/2011 | Cubb | |
| 7,997,468 B2 | 8/2011 | Farascioni | |
| 7,997,469 B2 | 8/2011 | Olson | |
| 8,105,233 B2 * | 1/2012 | Abou El Kheir | A61B 1/00097 600/173 |
| 8,123,795 B1 | 2/2012 | Knodel | |
| 8,186,555 B2 | 5/2012 | Shelton, IV | |
| 8,216,236 B2 | 7/2012 | Heinrich et al. | |
| 8,303,585 B2 | 11/2012 | Mollenauer | |
| 8,348,131 B2 | 1/2013 | Omaits | |
| 8,403,826 B1 | 3/2013 | Zobel | |
| 8,496,154 B2 | 7/2013 | Marczyk | |
| 8,523,043 B2 | 9/2013 | Ullrich et al. | |
| 8,579,178 B2 | 11/2013 | Holsten | |
| 8,647,258 B2 * | 2/2014 | Aranyi | A61B 1/0676 600/173 |
| 8,662,369 B1 | 3/2014 | Manoux | |
| 8,763,878 B2 | 7/2014 | Euteneuer | |
| 9,125,552 B2 * | 9/2015 | Dunki-Jacobs | A61B 5/0062 |
| 9,254,131 B2 | 2/2016 | Soltz | |
| 9,414,841 B2 | 8/2016 | Euteneuer | |
| 9,549,667 B2 | 1/2017 | Manohara | |
| 9,655,618 B2 | 5/2017 | Knodel et al. | |
| 9,707,043 B2 * | 7/2017 | Bozung | A61B 90/11 |
| 9,724,077 B2 * | 8/2017 | Aranyi | A61B 1/009 |
| 9,724,096 B2 | 8/2017 | Thompson | |
| 9,750,502 B2 | 9/2017 | Scirica | |
| 9,775,623 B2 | 10/2017 | Zammataro | |
| 9,844,324 B2 * | 12/2017 | Merritt | A61C 9/004 |
| 9,848,874 B2 | 12/2017 | Kostrzewski | |
| 9,872,683 B2 | 1/2018 | Hopkins et al. | |
| 9,888,832 B2 | 2/2018 | Schwartz | |
| 10,028,650 B2 | 7/2018 | Yoon | |
| 10,070,861 B2 * | 9/2018 | Spivey | A61B 1/0052 |
| 10,098,642 B2 | 10/2018 | Baxter, III | |
| 10,105,149 B2 * | 10/2018 | Haider | A61B 17/17 |
| 10,130,363 B2 | 11/2018 | Huitema | |

(56) References Cited

U.S. PATENT DOCUMENTS

| | | | |
|---|---|---|---|
| 10,188,275 B2 | 1/2019 | Sonnenschein et al. | |
| 10,201,365 B2* | 2/2019 | Boudreaux | A61B 90/06 |
| 10,219,811 B2* | 3/2019 | Haider | A61B 17/1764 |
| 10,245,038 B2 | 4/2019 | Hopkins et al. | |
| 10,278,778 B2 | 5/2019 | State | |
| 10,426,467 B2 | 10/2019 | Miller et al. | |
| 10,426,481 B2 | 10/2019 | Aronhalt | |
| 10,542,979 B2 | 1/2020 | Shelton, IV | |
| 10,555,775 B2* | 2/2020 | Hoffman | A61B 34/37 |
| 10,595,887 B2 | 3/2020 | Shelton, IV et al. | |
| 10,595,930 B2 | 3/2020 | Scheib et al. | |
| 10,624,616 B2 | 4/2020 | Mukherjee et al. | |
| 10,980,539 B2 | 4/2021 | Harris | |
| 11,020,111 B2 | 6/2021 | Euteneuer | |
| 11,045,267 B2 | 6/2021 | Hussain | |
| 11,090,045 B2 | 8/2021 | Shelton, IV | |
| 11,100,631 B2 | 8/2021 | Yates | |
| 11,116,574 B2* | 9/2021 | Haider | A61B 17/1703 |
| 11,291,510 B2 | 4/2022 | Shelton, IV | |
| 2001/0044656 A1 | 11/2001 | Williamson, IV | |
| 2001/0056282 A1* | 12/2001 | Sonnenschein | A61B 17/0686 |
| | | | 606/139 |
| 2002/0049367 A1 | 4/2002 | Irion | |
| 2002/0049472 A1 | 4/2002 | Coleman | |
| 2002/0183771 A1 | 12/2002 | Burbank | |
| 2003/0032863 A1* | 2/2003 | Kazakevich | A61B 1/00105 |
| | | | 600/173 |
| 2003/0144660 A1 | 7/2003 | Mollenauer | |
| 2003/0163029 A1* | 8/2003 | Sonnenschein | A61B 1/0051 |
| | | | 600/160 |
| 2004/0006372 A1 | 1/2004 | Racenet | |
| 2004/0138525 A1 | 7/2004 | Saadat | |
| 2005/0021010 A1* | 1/2005 | Rothweiler | A61B 1/313 |
| | | | 606/1 |
| 2005/0038317 A1 | 2/2005 | Ratnakar | |
| 2005/0080434 A1 | 4/2005 | Chung | |
| 2005/0090709 A1* | 4/2005 | Okada | A61B 17/072 |
| | | | 600/153 |
| 2005/0101974 A1 | 5/2005 | Burbank | |
| 2005/0119527 A1* | 6/2005 | Banik | A61B 1/0055 |
| | | | 600/117 |
| 2005/0182298 A1* | 8/2005 | Ikeda | A61B 34/70 |
| | | | 600/104 |
| 2005/0234296 A1* | 10/2005 | Saadat | A61B 1/0008 |
| | | | 600/173 |
| 2005/0288707 A1 | 12/2005 | De Canniere | |
| 2006/0020213 A1* | 1/2006 | Whitman | A61B 1/05 |
| | | | 600/478 |
| 2006/0111210 A1 | 5/2006 | Hinman | |
| 2006/0180633 A1 | 8/2006 | Emmons | |
| 2006/0191975 A1 | 8/2006 | Adams | |
| 2006/0229594 A1 | 10/2006 | Francischelli | |
| 2006/0235469 A1 | 10/2006 | Viola | |
| 2007/0005061 A1 | 1/2007 | Eder | |
| 2007/0055103 A1* | 3/2007 | Hoefig | A61B 1/00179 |
| | | | 600/137 |
| 2007/0073109 A1 | 3/2007 | Irion | |
| 2007/0175947 A1* | 8/2007 | Ortiz | A61B 17/07207 |
| | | | 227/175.1 |
| 2007/0194082 A1* | 8/2007 | Morgan | A61B 17/0682 |
| | | | 227/176.1 |
| 2007/0225562 A1* | 9/2007 | Spivey | A61B 1/0057 |
| | | | 600/121 |
| 2007/0244351 A1 | 10/2007 | Wazer | |
| 2007/0250102 A1* | 10/2007 | Makower | A61F 5/003 |
| | | | 606/192 |
| 2007/0262116 A1* | 11/2007 | Hueil | B25C 5/0292 |
| | | | 227/175.1 |
| 2007/0282356 A1 | 12/2007 | Sonnenschein | |
| 2008/0000941 A1 | 1/2008 | Sonnenschein | |
| 2008/0015618 A1 | 1/2008 | Sonnenschein | |
| 2008/0064921 A1 | 3/2008 | Larkin | |
| 2008/0065110 A1* | 3/2008 | Duval | A61B 1/00154 |
| | | | 606/130 |
| 2008/0065153 A1 | 3/2008 | Allard | |
| 2008/0082124 A1 | 4/2008 | Hess | |
| 2008/0151041 A1* | 6/2008 | Shafer | A61B 1/051 |
| | | | 348/E13.001 |
| 2008/0249565 A1 | 10/2008 | Michler | |
| 2008/0262302 A1* | 10/2008 | Azarbarzin | A61B 1/018 |
| | | | 604/93.01 |
| 2008/0269562 A1 | 10/2008 | Marescaux | |
| 2009/0054908 A1 | 2/2009 | Zand | |
| 2009/0054909 A1* | 2/2009 | Farritor | A61B 34/73 |
| | | | 606/130 |
| 2009/0062799 A1 | 3/2009 | Holsten | |
| 2009/0065552 A1 | 3/2009 | Knodel | |
| 2009/0069806 A1 | 3/2009 | De La Mora Levy | |
| 2009/0105815 A1 | 4/2009 | Krever | |
| 2009/0134194 A1 | 5/2009 | Maksimoski | |
| 2009/0182193 A1* | 7/2009 | Whitman | A61B 1/00131 |
| | | | 600/104 |
| 2009/0187072 A1* | 7/2009 | Manohara | A61B 1/00045 |
| | | | 600/109 |
| 2009/0250501 A1* | 10/2009 | Sonnenschein | A61B 17/072 |
| | | | 227/176.1 |
| 2009/0255976 A1 | 10/2009 | Marczyk | |
| 2009/0255978 A1 | 10/2009 | Viola | |
| 2009/0259097 A1* | 10/2009 | Thompson | A61B 1/018 |
| | | | 600/109 |
| 2009/0272783 A1 | 11/2009 | Crainich | |
| 2009/0277946 A1 | 11/2009 | Marczyk | |
| 2009/0277948 A1 | 11/2009 | Beardsley | |
| 2009/0281554 A1 | 11/2009 | Viola | |
| 2009/0292164 A1* | 11/2009 | Yamatani | A61B 17/00234 |
| | | | 600/106 |
| 2009/0318936 A1 | 12/2009 | Harris | |
| 2009/0326322 A1* | 12/2009 | Diolaiti | A61B 34/30 |
| | | | 600/112 |
| 2010/0072258 A1 | 3/2010 | Farascioni | |
| 2010/0100138 A1 | 4/2010 | Reynolds | |
| 2010/0114124 A1 | 5/2010 | Kelleher | |
| 2010/0127042 A1 | 5/2010 | Shelton, IV | |
| 2010/0191258 A1 | 7/2010 | Harris | |
| 2010/0191262 A1 | 7/2010 | Harris | |
| 2010/0234687 A1 | 9/2010 | Azarbarzin | |
| 2010/0237128 A1 | 9/2010 | Miller | |
| 2010/0249496 A1 | 9/2010 | Cardenas et al. | |
| 2010/0249499 A1 | 9/2010 | Whitman | |
| 2010/0249512 A1 | 9/2010 | McKinley | |
| 2010/0261961 A1* | 10/2010 | Scott | G02B 23/2476 |
| | | | 600/111 |
| 2010/0264192 A1 | 10/2010 | Marczyk | |
| 2010/0274087 A1* | 10/2010 | Diolaiti | A61B 90/361 |
| | | | 700/275 |
| 2010/0327042 A1 | 12/2010 | Amid | |
| 2011/0006104 A1 | 1/2011 | Felix | |
| 2011/0046666 A1 | 2/2011 | Sorrentino | |
| 2011/0063428 A1 | 3/2011 | Sonnenschein et al. | |
| 2011/0066231 A1 | 3/2011 | Cartledge | |
| 2011/0071508 A1* | 3/2011 | Duval | A61B 1/00087 |
| | | | 606/1 |
| 2011/0101069 A1 | 5/2011 | Bombard | |
| 2011/0112434 A1* | 5/2011 | Ghabrial | A61M 25/0133 |
| | | | 606/41 |
| 2011/0230894 A1* | 9/2011 | Simaan | A61B 1/05 |
| | | | 606/130 |
| 2011/0245578 A1 | 10/2011 | Wazer | |
| 2011/0288573 A1 | 11/2011 | Yates | |
| 2011/0295242 A1* | 12/2011 | Spivey | A61B 17/07207 |
| | | | 606/1 |
| 2012/0059394 A1 | 3/2012 | Brenner et al. | |
| 2012/0065494 A1 | 3/2012 | Gertner | |
| 2012/0078050 A1 | 3/2012 | Schwartz | |
| 2012/0080492 A1 | 4/2012 | Scirica | |
| 2012/0080503 A1* | 4/2012 | Woodard, Jr. | A61B 17/0643 |
| | | | 227/181.1 |
| 2012/0130403 A1 | 5/2012 | Brenner | |
| 2012/0143002 A1* | 6/2012 | Aranyi | A61B 1/042 |
| | | | 600/104 |

(56) References Cited

U.S. PATENT DOCUMENTS

| | | | |
|---|---|---|---|
| 2012/0160893 A1 | 6/2012 | Harris | |
| 2012/0199628 A1 | 6/2012 | Scirica | |
| 2012/0175401 A1 | 7/2012 | Bachnan | |
| 2012/0193398 A1 | 8/2012 | Williams | |
| 2012/0193399 A1 | 8/2012 | Holcomb | |
| 2012/0209318 A1 | 8/2012 | Qadeer | |
| 2012/0289781 A1 | 11/2012 | Pandey | |
| 2012/0296238 A1 | 11/2012 | Chernov | |
| 2013/0023868 A1* | 1/2013 | Worrell | A61B 17/07207 606/205 |
| 2013/0030438 A1 | 1/2013 | Fox | |
| 2013/0153628 A1 | 6/2013 | Euteneuer | |
| 2013/0233908 A1 | 9/2013 | Knodel | |
| 2013/0240595 A1 | 9/2013 | Penna | |
| 2013/0274712 A1 | 10/2013 | Schecter | |
| 2013/0306704 A1 | 11/2013 | Balbierz | |
| 2013/0345519 A1* | 12/2013 | Piskun | A61M 29/02 600/204 |
| 2014/0018613 A1* | 1/2014 | Scott | A61B 1/00193 600/102 |
| 2014/0021240 A1 | 1/2014 | Miyamoto | |
| 2014/0066911 A1 | 3/2014 | Nau, Jr. | |
| 2014/0107417 A1 | 4/2014 | McKinley | |
| 2014/0114327 A1 | 4/2014 | Boudreaux | |
| 2014/0135575 A1* | 5/2014 | Whitman | A61B 1/0669 600/104 |
| 2014/0142379 A1 | 5/2014 | Faehndrich | |
| 2014/0144968 A1 | 5/2014 | Shelton, IV | |
| 2014/0213848 A1* | 7/2014 | Moskowitz | A61B 17/29 600/106 |
| 2014/0236159 A1* | 8/2014 | Haider | A61B 17/1626 606/88 |
| 2014/0239037 A1 | 8/2014 | Boudreaux | |
| 2014/0263570 A1 | 9/2014 | Hopkins | |
| 2014/0275761 A1* | 9/2014 | Whitman | A61B 1/00174 600/102 |
| 2014/0318687 A1 | 10/2014 | Boettcher | |
| 2015/0066000 A1 | 3/2015 | An | |
| 2015/0122870 A1 | 5/2015 | Zemlok | |
| 2015/0238187 A1 | 8/2015 | Schellin | |
| 2015/0282749 A1* | 10/2015 | Zand | A61B 5/0084 600/301 |
| 2015/0297227 A1 | 10/2015 | Huitema | |
| 2015/0351758 A1 | 12/2015 | Shelton, IV | |
| 2015/0351765 A1 | 12/2015 | Valentine | |
| 2016/0000436 A1* | 1/2016 | Nicholas | A61B 17/105 227/176.1 |
| 2016/0051259 A1 | 2/2016 | Hopkins | |
| 2016/0066916 A1 | 3/2016 | Overmyer | |
| 2016/0073855 A1 | 3/2016 | Farr | |
| 2016/0089142 A1* | 3/2016 | Harris | A61B 17/105 606/219 |
| 2016/0100837 A1 | 4/2016 | Huang | |
| 2016/0135806 A1 | 5/2016 | Euteneuer | |
| 2016/0302791 A1 | 10/2016 | Schmitt | |
| 2016/0317157 A1 | 11/2016 | Bachar | |
| 2016/0345973 A1 | 12/2016 | Marczyk | |
| 2016/0345974 A1 | 12/2016 | Marczyk | |
| 2016/0367247 A1* | 12/2016 | Weaner | A61B 17/07207 |
| 2016/0367300 A1 | 12/2016 | Caldarella | |
| 2016/0374658 A1* | 12/2016 | Piskun | A61B 17/00234 600/204 |
| 2016/0374685 A1 | 12/2016 | Abbott | |
| 2017/0055819 A1* | 3/2017 | Hansen | A61B 17/062 |
| 2017/0056015 A1* | 3/2017 | Harris | A61B 17/07207 |
| 2017/0065276 A1 | 3/2017 | Weiner | |
| 2017/0112561 A1* | 4/2017 | Motai | A61B 17/07207 |
| 2017/0172550 A1 | 6/2017 | Mukherjee | |
| 2017/0231477 A1* | 8/2017 | Del Nido | A61B 17/3423 600/104 |
| 2017/0238991 A1 | 8/2017 | Worrell | |
| 2017/0245854 A1 | 8/2017 | Zemlok | |
| 2017/0296178 A1 | 10/2017 | Miller | |
| 2017/0354408 A1 | 12/2017 | Kostrzewski | |
| 2017/0367697 A1 | 12/2017 | Shelton, IV | |
| 2018/0028181 A1 | 2/2018 | Alzaga | |
| 2018/0042522 A1 | 2/2018 | Subramanian | |
| 2018/0059258 A1 | 3/2018 | MacLaughlin | |
| 2018/0092700 A1* | 4/2018 | Itkowitz | A61B 90/36 |
| 2018/0125570 A1 | 5/2018 | Rioux | |
| 2018/0235484 A1* | 8/2018 | Mozdzierz | A61B 17/29 |
| 2018/0235636 A1 | 8/2018 | Culbert | |
| 2018/0256161 A1 | 9/2018 | Eschbach | |
| 2018/0256163 A1 | 9/2018 | Evans | |
| 2018/0303314 A1* | 10/2018 | Noyes | A61B 1/00124 |
| 2019/0046220 A1 | 2/2019 | Chaturvedi | |
| 2019/0059894 A1 | 2/2019 | Kumada et al. | |
| 2019/0082932 A1 | 3/2019 | Schoonbaert | |
| 2019/0082944 A1 | 3/2019 | Fujimori | |
| 2019/0104919 A1 | 4/2019 | Shelton, IV | |
| 2019/0125458 A1 | 5/2019 | Shelton, IV | |
| 2019/0142589 A1 | 5/2019 | Basude | |
| 2019/0200863 A1 | 7/2019 | Shelton, IV | |
| 2019/0201141 A1* | 7/2019 | Shelton, IV | G16H 40/20 |
| 2019/0201146 A1 | 7/2019 | Shelton, IV | |
| 2019/0206551 A1* | 7/2019 | Yates | H04W 4/33 |
| 2019/0274531 A1* | 9/2019 | Maiorano | A61B 1/00066 |
| 2019/0321042 A1 | 10/2019 | Marczyk | |
| 2019/0321044 A1 | 10/2019 | Franklin, Sr. | |
| 2019/0328390 A1* | 10/2019 | Harris | A61B 17/0644 |
| 2020/0015847 A1 | 1/2020 | Pedreira de Cerqueira Filho | |
| 2020/0015897 A1 | 1/2020 | Scheib | |
| 2020/0029948 A1 | 1/2020 | Wong | |
| 2020/0037858 A1 | 2/2020 | Pedreira de Cerqueira Filho | |
| 2020/0100776 A1 | 4/2020 | Blumenkranz | |
| 2020/0214703 A1 | 7/2020 | Thompson et al. | |
| 2021/0177402 A1 | 6/2021 | Vyas | |
| 2021/0177403 A1 | 6/2021 | Vyas | |
| 2021/0177404 A1 | 6/2021 | Vyas | |
| 2021/0177405 A1 | 6/2021 | Vyas | |
| 2021/0186511 A1 | 6/2021 | Shellenberger | |
| 2022/0008068 A1* | 1/2022 | Vyas | A61B 1/018 |

\* cited by examiner

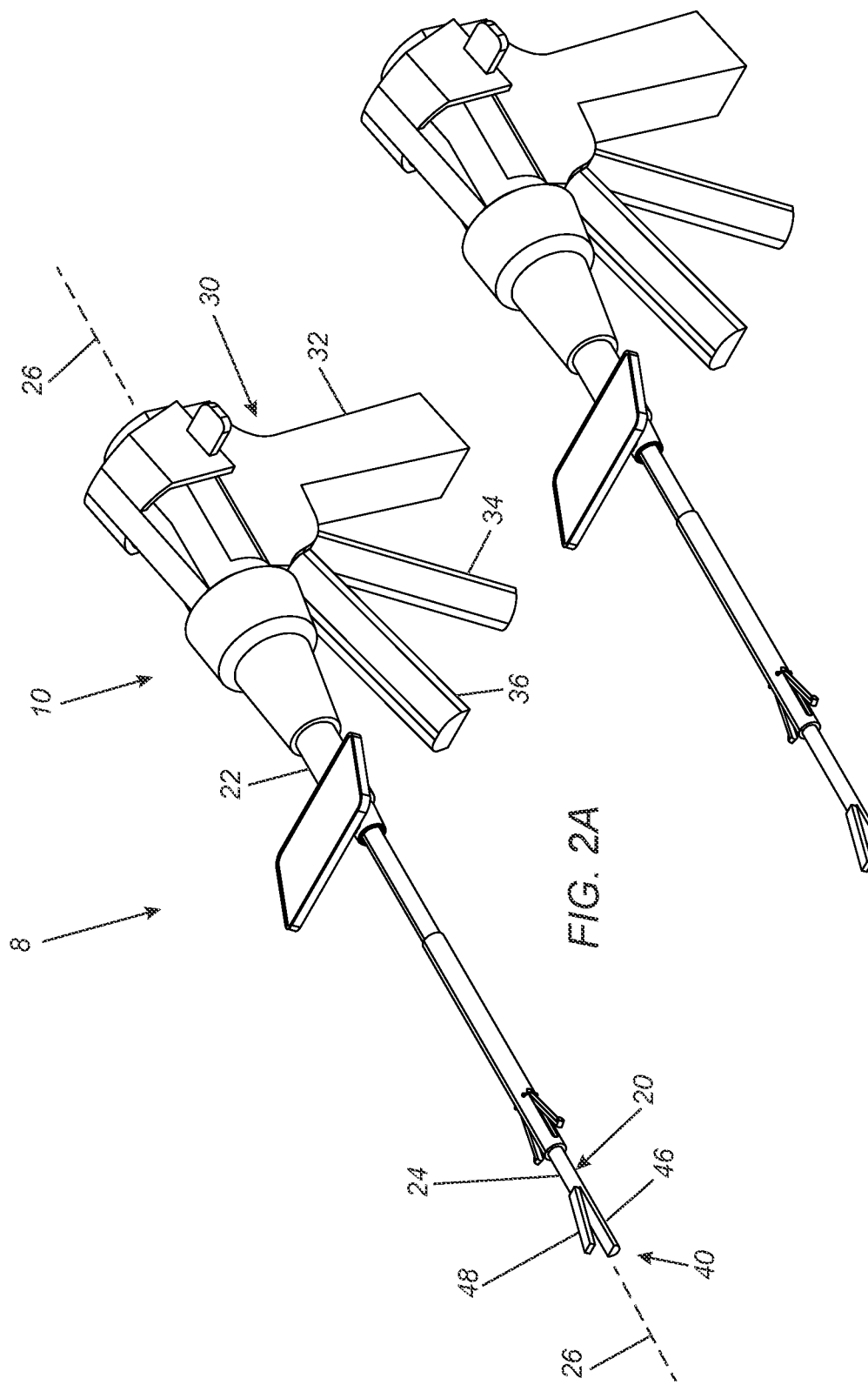

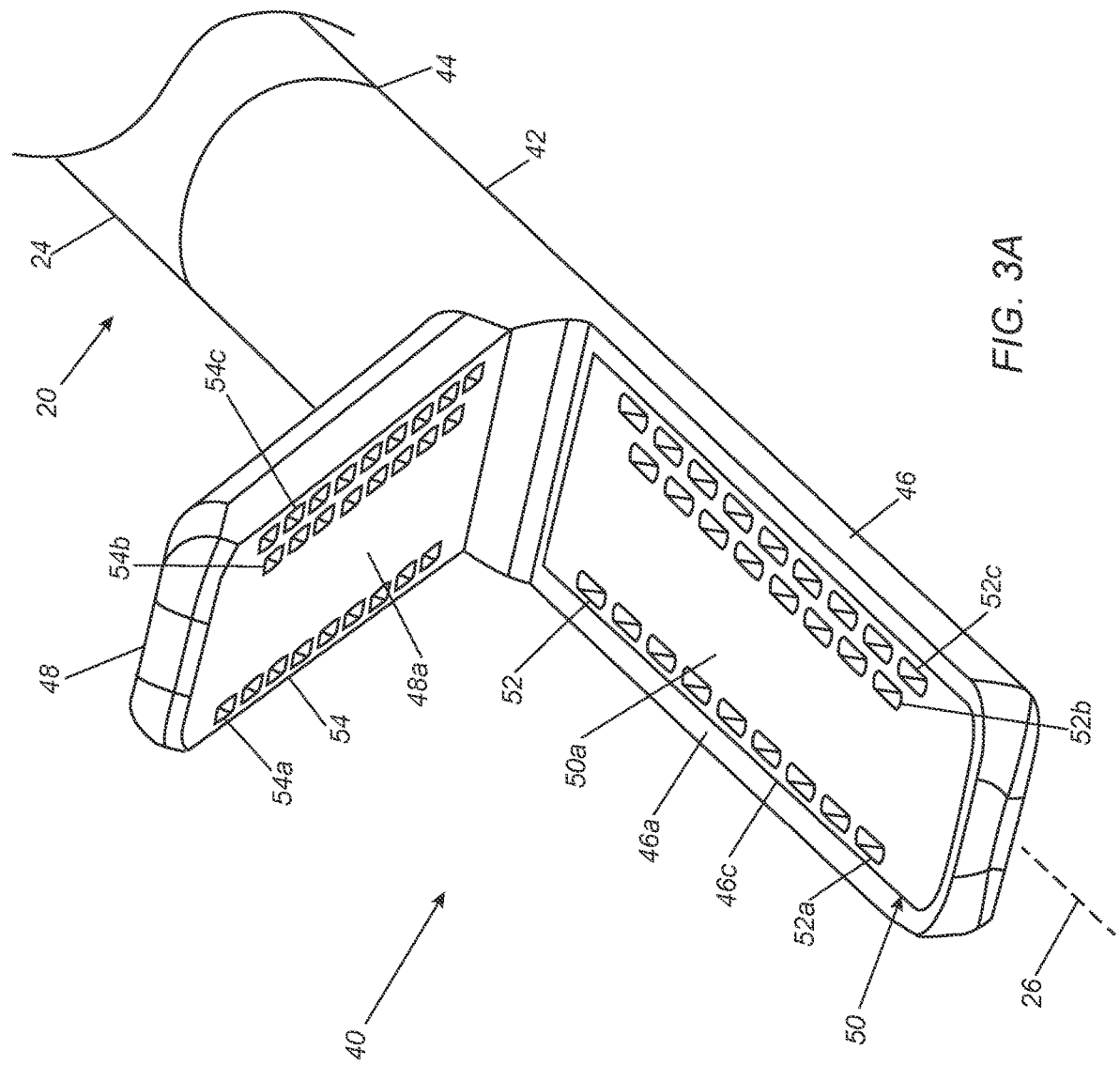

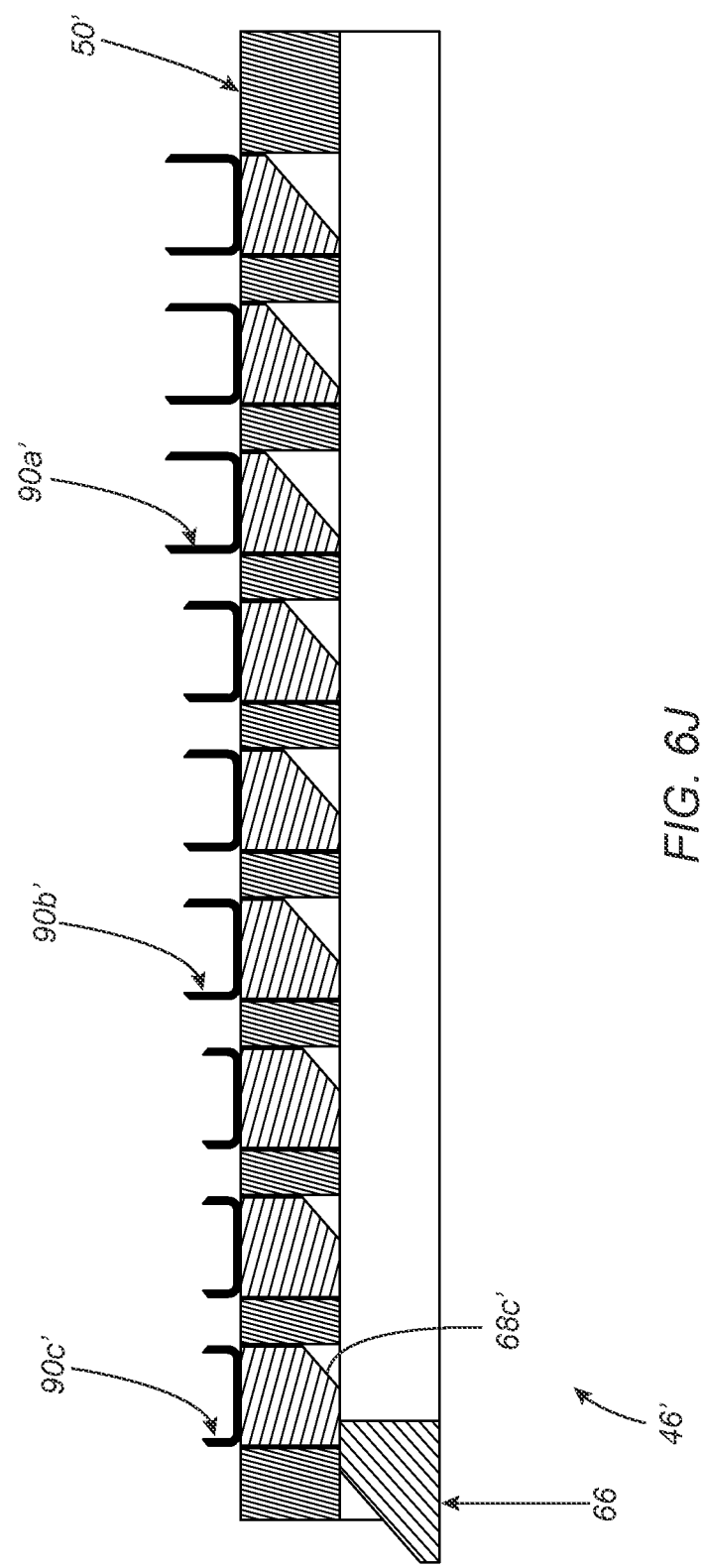

STAPLER APPARATUS AND METHODS FOR USE

RELATED APPLICATION DATA

The present application is a continuation-in-part of co-pending application Ser. No. 16/874,618, filed May 14, 2020, which claims benefit of U.S. provisional application Ser. No. 62/947,903, filed Dec. 13, 2019.

FIELD OF THE INVENTION

The present application relates generally to apparatus, systems, and methods for performing medical procedures, and, more particularly, to stapler apparatus for performing laparoscopic or other surgery, e.g., to perform an appendectomy or tubal ligation on a subject, and to systems and methods for using such apparatus.

BACKGROUND

Appendicitis is seen in approximately 5-10% of the population in their life time. Since 1983, laparoscopic appendix surgery is the mainstay for treatment. In an example of conventional surgery to remove an appendix, the following steps may be performed. First, the appendix and its vessel may be initially identified e.g., lying within a fold of tissue called the mesoappendix. A window or surgical field may be created within the subject's body, and a stapler apparatus is then used, e.g., to initially staple and divide the structure closest to the operator, and then to staple and divide the remaining structure.

For example, FIG. 1 shows exemplary anatomy of an appendix, which may have one of a variety of orientations relative to the intestine, most commonly retrocecal (64%) or pelvic (32%), although less common positions may also be encountered, as shown. An appendicular artery and other blood vessels (not shown) deliver blood to the appendix, whose location relative to the intestine may also vary depending on the orientation of the appendix. The appendix and artery may be separated by fat and/or other tissue. Thus, during a procedure, upon accessing the abdominal cavity, the operator must identify the relative locations of the appendix and vessels before removing the appendix. For example, after identification, the operator may identify the intra-operative manifestation or positioning of the appendix and its vessel, i.e., to identify whether the appendix is closer to the operator and the vessel is positioned further away or vice-versa, and then sequentially staple and divide the closer structure, and then the more distant structure.

To perform laparoscopic or open surgery, a device may be introduced carrying a camera that is independent from the stapler, e.g., to enable visualization of the surgical space and anatomy from the side, e.g., when the stapler is introduced and used to remove the appendix. Existing laparoscopic staplers generally include a cartridge having multiple rows of staples equally distributed on either side of a knife.

One of the most common complications from such surgery is post-operative bleeding. The bleeding is generally sub-clinical in approximately 15%, and clinical in approximately 5% patients, i.e., requiring further intervention. The majority of bleeding occurs from the staple line on individual vessels or vessels within the wall of intestine. For example, "B" shaped clips may create a lumen between the tines that may allow blood or other fluid to escape. Other complications include leaking of intestinal fluid from the intestinal lumen.

Accordingly, apparatus and methods that facilitate laparoscopic surgery, e.g., to remove an appendix would be useful.

SUMMARY

The present application is directed to apparatus, systems, and methods for performing medical procedures, and, more particularly, to stapler apparatus for performing surgery, such as laparoscopic surgery, e.g., to remove an appendix of a subject or to perform a tubal ligation, lung biopsy, ovary removal, or liver cyst removal, and to systems and methods for using such apparatus.

In accordance with one example, an apparatus is provided for performing a medical procedure that includes a shaft including a proximal end, a distal end sized for introduction into a patient's body, and a longitudinal axis extending between the proximal and distal ends; first and second jaws on the distal end of the shaft that are movable relative to one another between open and closed positions, thereby directing first and contact surfaces of the first and second jaws away from and towards one another, respectively, the first jaw carrying first and second sets of staples positioned in rows parallel to the longitudinal axis, wherein at least some of the staples are a different size than other staples; and a handle on the proximal end of the shaft. For example, each set of staples may include one to ten axial rows of staples aligned along the longitudinal axis, with two to fifty staples in each row. The staples in each set and/or each row may have different sizes depending on the anatomy encountered. For example, the apparatus may include a plurality of available cartridges, each including different arrangements of staples, that may be selected and inserted into a cavity of the first jaw. The handle includes a first actuator for opening and closing the jaws, and a second actuator for driving the staples from the first jaw into tissue between the first and second contact surfaces and towards the second jaw to deform the staples.

In accordance with yet another example, an end effector is provided for a stapler apparatus including a shaft comprising a proximal end including a handle, a distal end sized for introduction into a patient's body, and a longitudinal axis extending between the proximal and distal ends. The end effector may include one or more connectors for removably connecting the end effector to the distal end of the shaft; first and second jaws that are movable relative to one another between open and closed positions using a first actuator on the handle, thereby directing first and contact surfaces of the first and second jaws away from and towards one another, respectively; and a cartridge carried by the first jaw comprising first and second sets of staples arranged in rows parallel to the longitudinal axis such that actuation of a second actuator on the handle deploys the staples into tissue between the first and second contact surfaces and drives the staples against the second jaw to deform the one or more staples, wherein at least some of the staples are a different size than other staples.

In accordance with another example, an imaging system is provided for use with a stapler apparatus that includes an elongate tubular member comprising a proximal end, a distal end sized for introduction into a patient's body, and a lumen extending between the proximal and distal ends for receiving a shaft of the stapler apparatus, thereby defining a longitudinal axis there between; a display; and one or more deployment arms on the tubular member adjacent the distal end carrying an imaging device, each deployment arm comprising a first end pivotably coupled to the tubular member and a second free end that is movable from a retracted position wherein the second end is aligned with a wall of the tubular member and a deployed position wherein the second end moves outwardly relative to the longitudinal axis for presenting images on the display.

In accordance with still another example, a system is provided for performing a medical procedure that includes a shaft including a proximal end, a distal end sized for introduction into a patient's body, and a longitudinal axis extending between the proximal and distal ends; first and second jaws on the distal end of the shaft that are movable relative to one another between open and closed positions, thereby directing first and contact surfaces of the first and second jaws away from and towards one another, respectively, the first jaw carrying first and second sets of staples positioned in rows parallel to the longitudinal axis; and an imaging sleeve carried on the shaft including a tubular member carrying a display, and one or more deployment arms on the tubular member adjacent the end effector end carrying an imaging device coupled to the display. In one example, each deployment arm includes a first end pivotably coupled to the tubular member and a second free end that is movable from a retracted position wherein the second end is aligned with a wall of the tubular member and a deployed position wherein the second end moves outwardly relative to the longitudinal axis for presenting images on the display.

Other aspects and features of the present invention will become apparent from consideration of the following description taken in conjunction with the accompanying drawings.

BRIEF DESCRIPTION OF THE DRAWINGS

The drawings illustrate examples of the invention, in which:

FIGS. 2A and 2B are perspective views of an exemplary stapler apparatus including a handle portion including a shaft extending from a handle, an end effector coupled to the shaft, and an integral imaging sleeve carrying a display that is movable between extended (FIG. 2A) and retracted positions (FIG. 2B).

FIGS. 3A and 3B are perspective and side views, respectively, of an exemplary end effector that may be provided on the shaft of the apparatus of FIGS. 2A and 2B, the end effector including a first jaw carrying a plurality of staples within a cartridge and a second jaw pivotable relative to the first jaw between an open position (FIG. 3A) and a closed position (FIG. 3B).

FIGS. 6A-6J are cross-sections of a jaw including a cartridge carrying a plurality of different size staples showing deployment of the staples.

DETAILED DESCRIPTION

Figure 1:
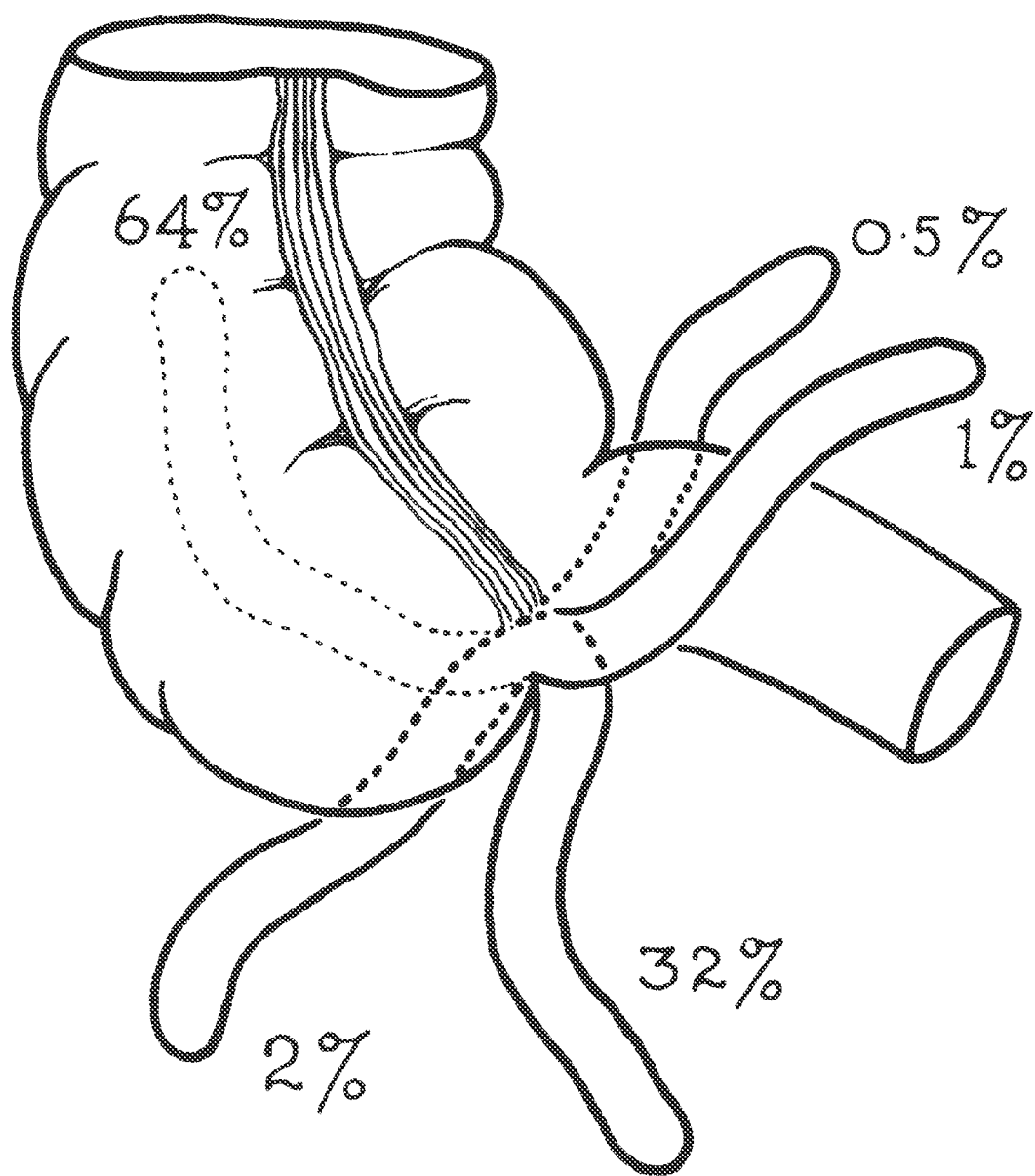
FIG. 1 is a detail showing exemplary anatomy of an appendix, which may have a variety of orientations relative to the intestine.

Before the examples are described, it is to be understood that the invention is not limited to particular examples described, as such may, of course, vary. It is also to be understood that the terminology used herein is for the purpose of describing particular examples only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described.

It must be noted that as used herein and in the appended claims, the singular forms "a," "an," and "the" include plural referents unless the context clearly dictates otherwise. Thus, for example, reference to "a compound" includes a plurality of such compounds and reference to "the polymer" includes reference to one or more polymers and equivalents thereof known to those skilled in the art, and so forth.

Turning to the drawings, FIG. 2A shows an example of a stapler apparatus 8 that may be used during a medical procedure, e.g., during laparoscopic surgery to remove a patient's appendix, remove an ovary, resect a liver cyst, perform a tubal ligation or lung biopsy, and the like (not shown). Generally, the apparatus 8 includes a shaft/handle portion or handpiece 10 including a shaft 20 and a handle 30, an end effector or stapler assembly 40, e.g., configured to receive a single-use cartridge (not shown), which may be removably coupled to the shaft 20 before or during a procedure, and an integral imaging assembly 70, as described further below. Alternatively, at least some of the components of the end effector 40 may be permanently incorporated into the reusable portion 10, e.g., such that the entire apparatus 8 may be single-use or may be cleaned between procedures and reused.

As shown, the shaft 20 is an elongate member, e.g., a substantially rigid tubular body, including a proximal end 22 and a distal end 24, defining a longitudinal axis 26 extending there between. The shaft 20 may include one or more lumens or passages (not shown) extending between the proximal and distal ends 22, 24, e.g., for receiving actuator elements, wires, and/or other components, as described elsewhere herein. At least the distal end 24 of the shaft 20 is sized for introduction into a patient's body, e.g., having a diameter sufficiently small enough to be received through a port or cannula to allow introduction into a laparoscopic surgical space within a patient's body.

Optionally, at least a portion of the shaft 20 may be malleable, e.g., such that at least a distal region of the shaft 20 may be deformed into a desired shape outside the patient's body, which the shaft 20 may maintain during introduction. Alternatively, at least a distal region of the shaft 20 and/or the end effector 40 may be flexible, e.g., for introduction into body passages, such as blood vessels, GI passages, and the like, such that the distal region follows the passages during introduction. Optionally, in this alternative, the shaft 20 may include one or more steering wires or other elements therein (not shown) that may be actuated to change the shape of the shaft 20, e.g., to facilitate introduction into a desired location and/or manipulation within the patient's body.

The handle 30 may include a handgrip 32, e.g., shaped and/or otherwise configured to facilitate holding and/or manipulating the apparatus 8 during use. In addition, the handle 30 may include one or more actuators, e.g., for operating mechanical components on the end effector 40. For example, a trigger or other jaw actuator 34 may be provided, e.g., adjacent the handgrip 32, that may be pulled or otherwise actuated to open and/or close jaws 46, 48 and a separate actuator 36 may be provided to subsequently deploy one or more staples (not shown) from the end effector 40. For example, the trigger 34 may be pulled to close the second jaw 48 immediately adjacent the first jaw 46 to engage tissue between contact surfaces 46a, 48a, e.g., as described further elsewhere herein. Optionally, the trigger 34 may include a ratchet mechanism to allow the second jaw 48 to move towards the first jaw 46 while preventing opening, e.g., to squeeze tissue between the jaws 46, 48, e.g., until a release mechanism is actuated. Alternatively, a separate locking mechanism may be provided on the handle 30, which may be selectively activated to lock and release the second jaw 48, as described elsewhere herein.

In addition, the apparatus 8 includes an imaging assembly or sleeve 70, e.g., carried on the shaft 20 that, in turn carries a display or other output device 82, e.g., to facilitate observing or otherwise monitoring the procedure. For example, as described further below, the imaging sleeve 70 may include one or more cameras and/or other imaging elements (not shown), e.g., carried on deployment arms 82, that may be used to acquire images of a surgical space into which the end effector 40 is introduced, as described further elsewhere herein. For example, a CMOS, CCD, or other imaging element (not shown) may be provided on each arm 82 that is oriented to acquire images of the region beyond the end effector 40 and/or between jaws 46, 48 of the end effector 40. One or more wires and/or optical fibers (not shown) may transmit signals to the display 82, which, optionally, may include a processor (also not shown) to process the signals and present the images on a screen of the display 38. In addition or alternatively, one or more LEDs or other light sources may be provided on one or both arms 82, e.g., adjacent the imaging element(s) to provide illumination for the images. The handle 30 and/or display 82 may include one or more controls (not shown), e.g., to turn the illumination source(s) and/or imaging element(s) off and on, as desired. Optionally, the imaging sleeve 70 may be movable relative to the end effector 40, e.g., slidably axially between an extended position, as shown in FIG. 2A and a retracted position, as shown in FIG. 2B, which may facilitate focusing the imaging element(s) and/or increasing or reducing the field of view during a procedure, as described further elsewhere herein.

Figure 3B:
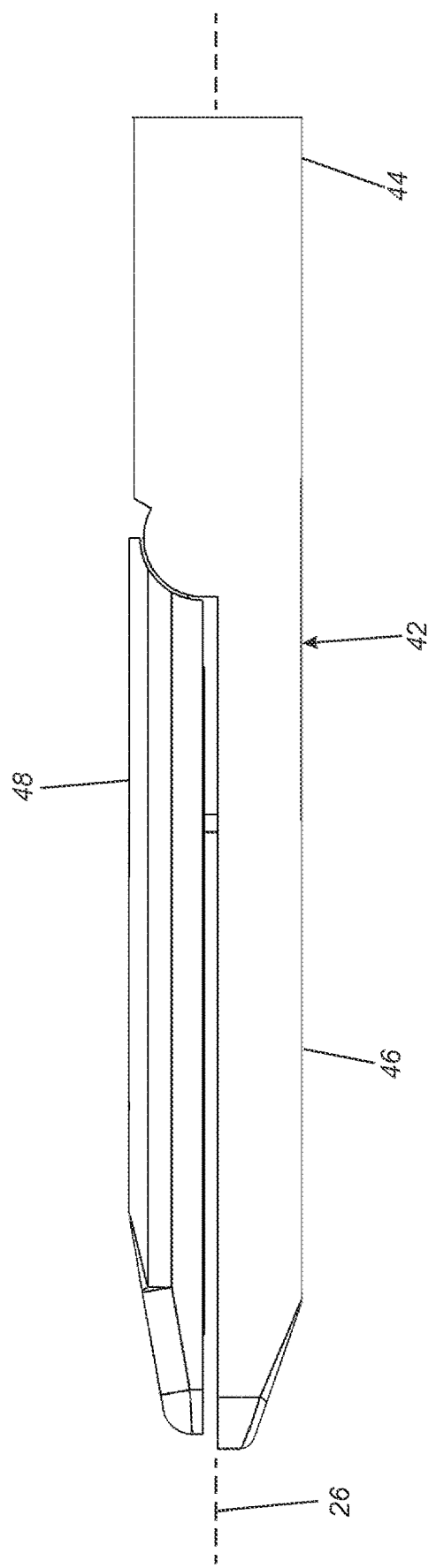

With additional reference to FIGS. 3A and 3B, generally, the end effector 40 on the distal end 24 of the shaft 20 includes first and second jaws 46, 48 carrying one or more staples (not shown). For example, as shown in FIG. 3A, the end effector 40 may include a removable cartridge 50 receivable within a recess, track, or other cavity 46c within the first jaw 46. The end effector 40 may also include a tubular housing 42 from which the first jaw 46 extends that includes a proximal end 44 that may be connected to the distal end 24 of the shaft 20, e.g., using one or more detents, latches, sockets, threads and/or other connectors (not shown) on the proximal end 44 of the housing 40 and/or the distal end 24 of the shaft 20. When the end effector 40 is mechanically connected to the shaft 20 by the connector(s), additional connectors may automatically engage, e.g., to mechanically couple actuatable components on the end effector 40 with actuator elements in the shaft 20, as will be appreciated by those skilled in the art. For example, a wedge mechanism 66 (not shown, see, e.g., FIGS. 5A-5D) may be provided within the housing 42 adjacent the first jaw 46 that may be coupled to an actuator shaft 28 within the shaft 20 such that actuation of the staple actuator 36 on the handle 30 may be activated to advance and retract the actuator shaft 28 and wedge 66 to deliver the staples, as described elsewhere herein.

As shown, the first jaw 46 may be integrally formed with or otherwise fixed relative to the housing 42, e.g., such that the first jaw 46 remains aligned with the longitudinal axis 26 of the shaft 20 during use. The second jaw 48 may be movably mounted to the housing 42, e.g., by one or more hinges or other features (not shown) such that the second jaw 48 may be pivotable between an open position, e.g., as shown in FIG. 3A, and a closed position, e.g., as shown in FIG. 3B. In the open position, contact surfaces 46a, 48a of the jaws 46, 48 may be spaced apart from one another, e.g., to allow a tissue structure to be positioned between the jaws 46, 48, e.g., on the first contact surface 46a, while in the closed position, the contact surfaces 461, 48b may be immediately adjacent one another, e.g., substantially parallel to one another, as shown in FIG. 3B. For example, in the closed position, the contact surfaces 46a, 48a may have sufficient clearance between them to squeeze, secure, and/or otherwise engage tissue positioned between the jaws 46, 48.

The jaws 46, 48 may be biased to one of the open and closed positions or may be actuatable between the open and closed positions. For example, the jaws 46, 48 may be provided initially in a closed position, e.g., to facilitate introduction into a patient's body, whereupon a lock or other release mechanism may be released, whereupon the second jaw 48 may automatically move to the open position, and the jaw actuator 34 on the handle 30 may become active to close the second jaw 48 and deploy staples, as described further elsewhere herein.

With particular reference to FIG. 3A, the first jaw 46 may receive a disposable cartridge 50 which may be received in cavity 46c of the first jaw 46 such that an exposed surface 50a of the cartridge 50 defines at least a portion of the first contact surface 46a. The cartridge 50 may carry a plurality of staples (not shown), e.g., arranged in a plurality of rows aligned with the longitudinal axis 26 of the shaft 20. For example, in the example shown in FIG. 3A, the contact surface 50a of the cartridge 50 includes recesses or receptacles 52 arranged in three rows 52a, 52b, 52c from which staples may be deployed simultaneously and/or in rapid succession.

In the example shown in FIG. 3A, a first row or set of staple receptacles 52a may be located on the right side of the cartridge 50 (from the perspective of a user holding the handle 30 of the apparatus 8), and second and third rows or sets of staple receptacles 52b, 52c may be located on the left side of the cartridge 50, i.e., spaced apart from the first row 52a. For example, in this configuration, the first set of staples may be delivered into the appendix being removed, while the second set of staples may be delivered into the intestine and remain within the patient's body after the appendix is removed. Alternatively, the arrangement of the receptacles 52 may be reversed if desired, e.g., with the first set on the left and the second set on the right for approaches where the appendix is on the left (from the perspective of the operator of the apparatus 8) and the intact intestine is on the right. As shown, the second set of receptacles 52b, 52c may include two rows of staples that are staggered relative to one another along the longitudinal axis 26, e.g., to enhance stapling a tissue structure captured in the jaws 46, 48, as described elsewhere herein.

In the example shown in FIG. 3A, the receptacles 52 have similar dimensions, e.g., having the same length aligned with the axis 26, and the staples deployable from the receptacles 52 may have the same dimensions. Alternatively, the dimensions of the receptacles and, consequently, the staples, may be varied along each row and/or in different rows, as described further elsewhere herein.

For example, the rows of staple receptacles may include a first or proximal set of receptacles and a second or distal set of receptacles that have different sizes. For example, the first/proximal set of receptacles in each row may be larger than the remaining receptacles. In this alternative, when the staples are deployed, the larger, proximal staples will be deployed first followed by the smaller, distal staples, e.g., as the staple actuator (e.g., a piston and/or sledge, not shown) advances and the pushes the staples against the second jaw 48 (also not shown) to deform the deployed staples. FIGS. 6A-6J show an alternative example of a first jaw 46' and cartridge 50' where the cartridge 50' includes a row of receptacles 52' in which the receptacles 52' have the same length along the longitudinal axis 26' and different depths. In this specific example, a first or proximal set of receptables 52a' that have a first depth, a second or central set of receptacles 52b' that have a second depth less than the first depth, and a third or distal set of receptacles 52c' that have a third depth less than the second depth. Consequently, staples 90' received in the receptacles 52' may have similar widths but different tine lengths, as described further elsewhere herein.

Alternatively, different size staples may be provided in one or more of the rows on the first jaw. For example, the first row 52a may include receptacles that are larger than the second and third rows (not shown) of receptacles 52b, 52c. Consequently, larger staples may be deployed from the first row of receptacles 52a than the others. For example, it may be desirable to use larger staples to staple an appendix while smaller staples may be used to staple the blood vessel delivering blood to the appendix. Many smaller staples may enhance cutting off blood flow to the vessel, which may reduce risk of subsequent bleeding when the appendix is severed and removed. Thus, cartridges may be provided with multiple rows on either the left or right side and with larger staples on the other side such that an appropriate cartridge may be selected and connected to the handpiece 30 based on the actual anatomy encountered. Optionally, one or more additional rows or sets of staples may be provided adjacent the first, second, and/or third rows. For example, multiple sets of staples may be delivered into the appendix being removed and/or into the intestine.

Returning to FIG. 3A, the contact surface 48a of the second jaw 48 may include corresponding recesses 54, e.g., arranged in rows opposite the receptacles 52, e.g., such that the recesses 54 are disposed directly above respective receptacles 52 in the closed position, e.g., to deform and/or otherwise close staples deployed from the receptacles 52, as described further elsewhere herein. For example, the recesses 54 may include ramped surfaces, anvils, and/or other features (not shown) to deform one or both of the tines of the staples as they are deployed, as described further elsewhere herein.

Turning to FIGS. 4A-4E, an example of the imaging sleeve 70 is shown that generally includes an elongate tubular body 72 including a proximal end 74, a distal end 76 sized for introduction into a patient's body, and one or more lumens or passages 78 extending at least partially between the proximal and distal ends 74, 76. For example, the tubular body 72 may include a primary lumen 78a sized to receive the shaft 20 of the handpiece 10. The length of the tubular body 72 may be shorter than the length of the shaft 20, e.g., such that the tubular body 72 may be slidable axially on the shaft 20, e.g., between the extended and retracted positions shown in FIGS. 2A and 2B. Alternatively, the tubular body 72 may be axially fixed and/or rotatable relative to the shaft 20 or the tubular body 72 (and consequently the entire imaging assembly 70) may be removable from the shaft 20. For example, the tubular body 72 may be received over the distal end 24 of the shaft 20, e.g., before connecting an end effector 40 to the distal end. In addition, the tubular body 72 may include one or more secondary lumens (not shown), e.g., extending at least partially from the proximal end 74 towards the distal 76, e.g., for receiving actuator elements, wires, and/or other components, as described elsewhere herein. The tubular body 72 may be substantially rigid or alternatively at least a portion of the tubular body 72, e.g., a distal portion, may be malleable or flexible (not shown).

A hub 80 may be provided on the proximal end 74, e.g., to facilitate manipulation of the imaging sleeve 70 during use. In addition, a display or other output device 82 may be provided on the hub 80, e.g., to facilitate observing or otherwise monitoring the procedure using one or more imaging devices on the imaging sleeve 80. For example, a distal portion of the tubular body 72 may include a pair of deployable arms 84 including first ends 84a pivotally coupled to the tubular body 72 and second or free ends 84b that may carry one or more cameras, light sources, and/or other imaging elements, as described further below.

In one example, the display 82 may be removably mountable on the hub 80, which may include one or more connectors or cables (not shown) that may be coupled to corresponding connectors on the hub 80, which are, in turn, coupled to one or more wires extending to the imaging device(s) on the arms 84. Thus, in this alternative, the display 82 may be reusable and the independent of the imaging sleeve 70 and handpiece 10. Alternatively, the display 82 may be permanently mounted to the hub 80 and one or more wires or other elements may communicate with the imaging device(s). Thus, in this alternative, the entire imaging sleeve 70 may cleaned and reused along with the handpiece 10 or the entire apparatus 8 may be single-use.

In one example, a CMOS, CCD, or other imaging element (not shown) may be provided on the free end 84b of one of the arms 84 and one or more LEDs or other light sources may be provided on the free end 84b of the other arm 84. Alternatively, separate light sources and imaging elements may be provided on both arms, e.g., to provide multiple images simultaneously on the display 82. In a further alternative, only one arm may be provided, if desired, including one or more light sources and/or imaging elements on its free end.

In any of these examples, one or more wires may transmit signals from the imaging element(s) to the display 82, which may include a processor to process the signals and present the images on a screen of the display 82. The imaging element(s) may include a field of view oriented distally beyond the distal end 76 of the tubular body 72, e.g., to illuminate and/or image an instrument deployed within a region beyond the distal end 76.

Figure 4A:
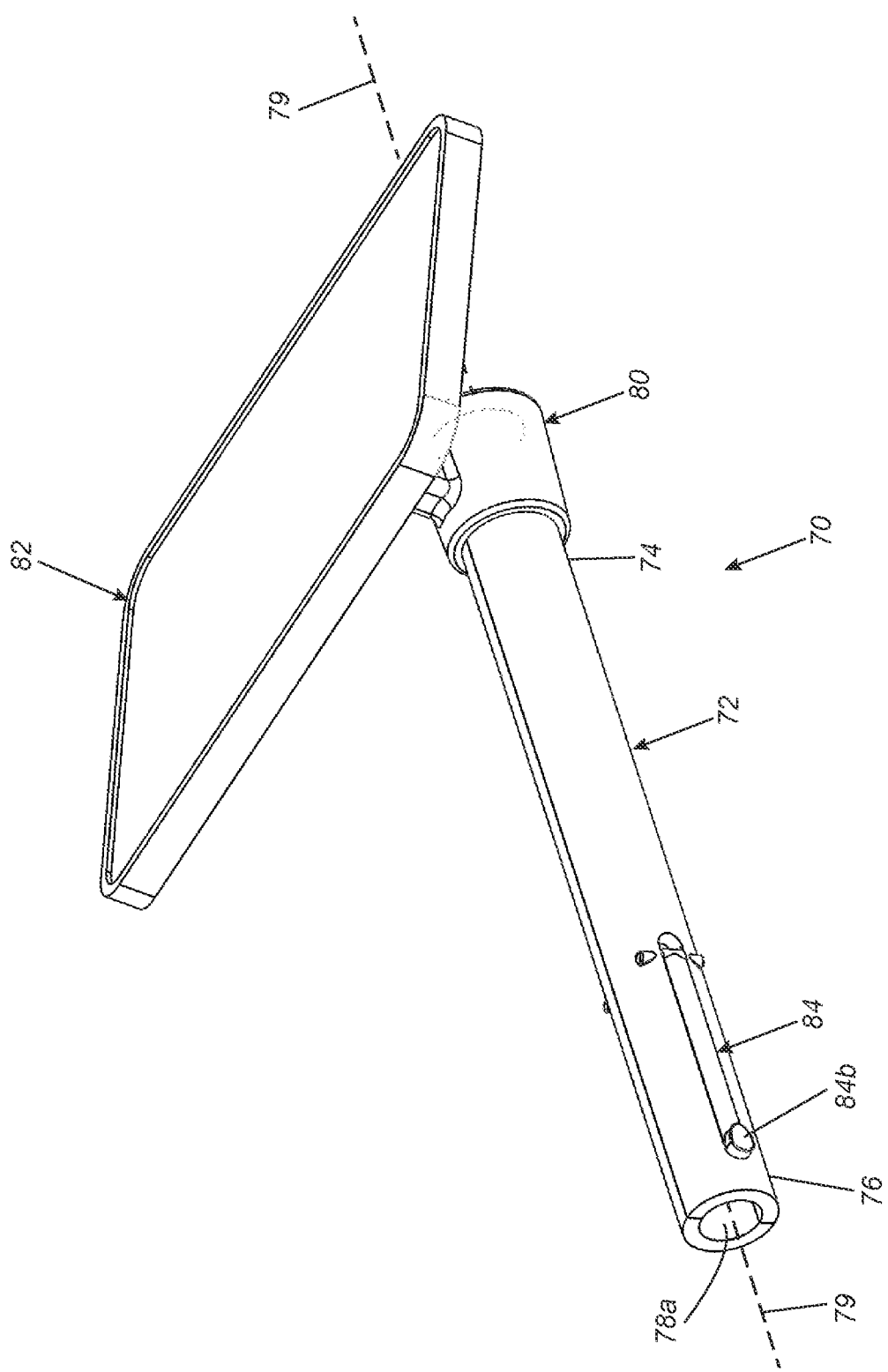
FIGS. 4A and 4B are perspective views of an exemplary imaging sleeve including a tubular shaft carrying a deployable imaging system carried on deployment arms movable between retracted and deployed configurations, respectively.
Figure 4B:
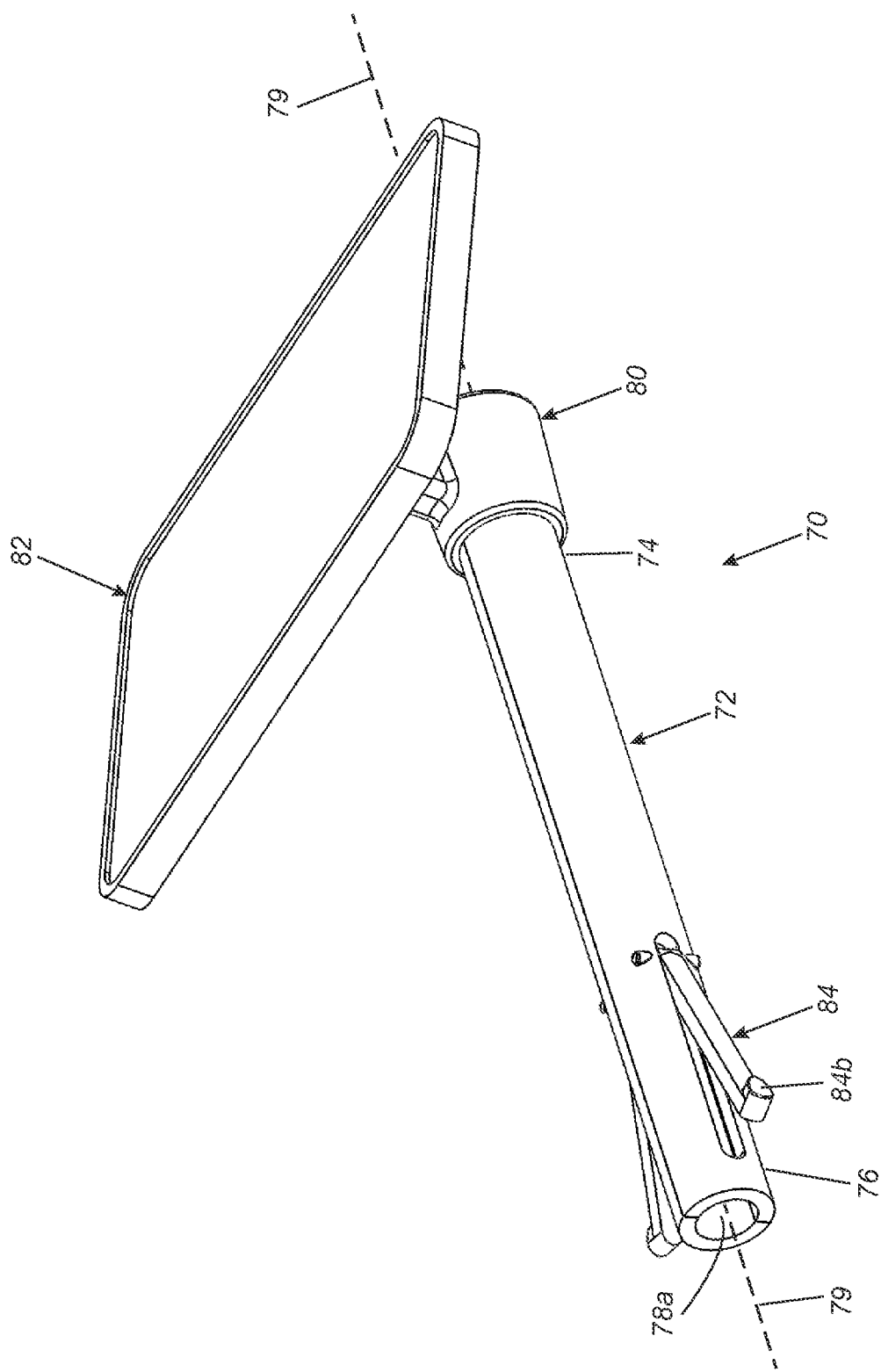
Figure 4C:
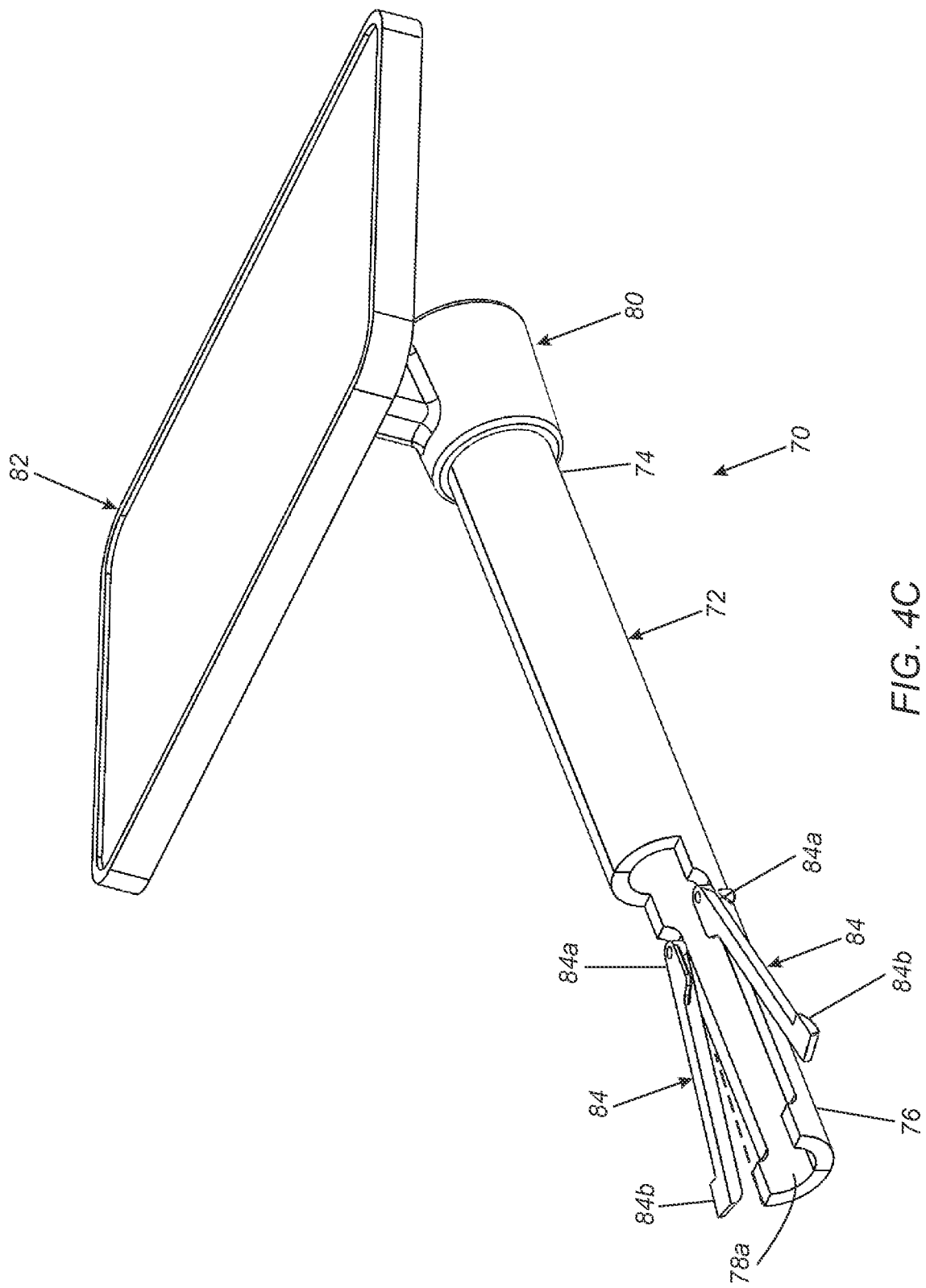
FIG. 4C is a perspective view of the imaging sleeve of FIGS. 4A and 4B with a portion of the tubular shaft removed to show details of the deployment arms of the imaging system.
Figure 4D:
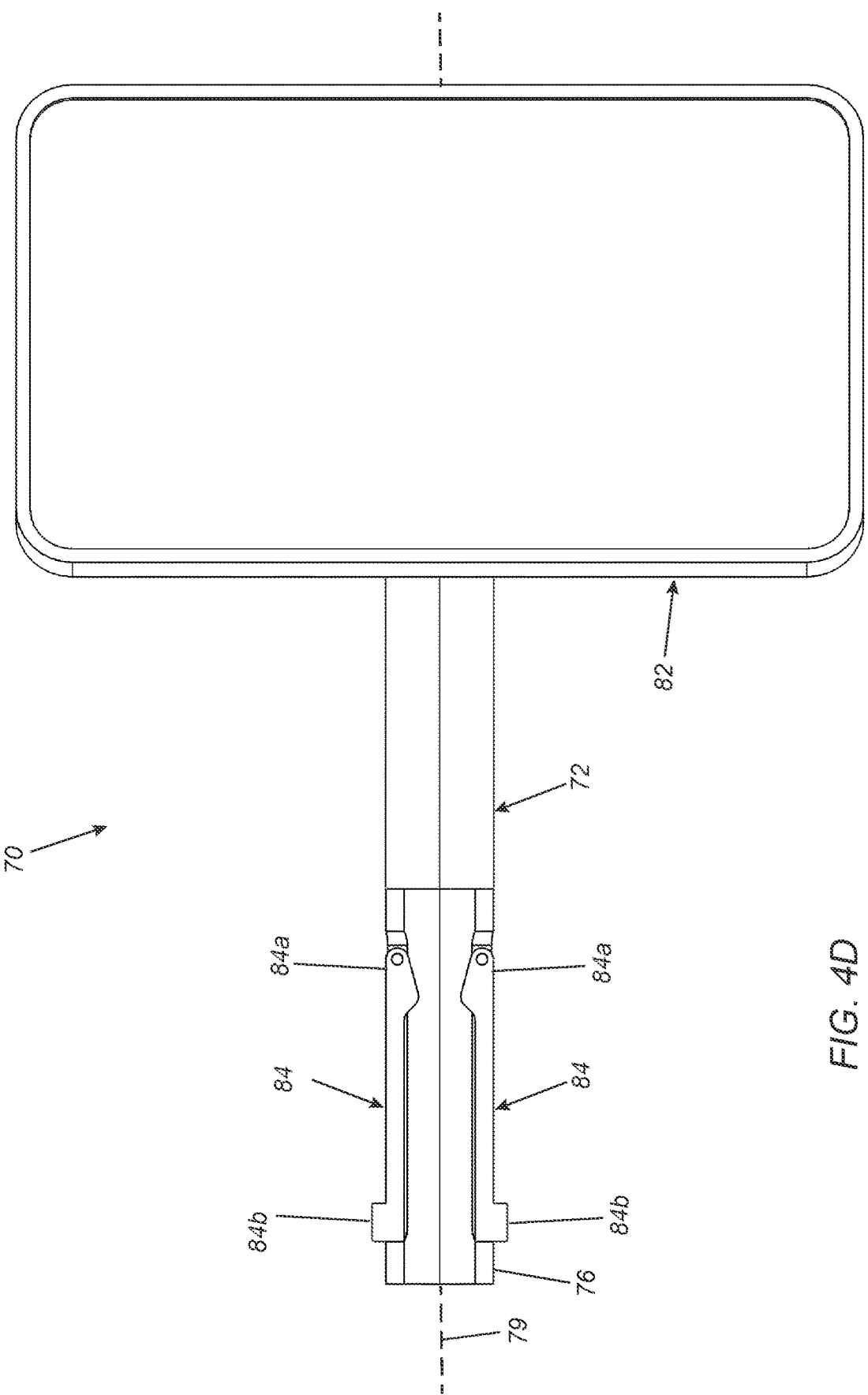
FIGS. 4D and 4E are top views of the imaging sleeve of FIGS. 4A and 4B, respectively, with a portion of the tubular shaft removed to show details of the deployment arms of the imaging system.
Figure 4E:
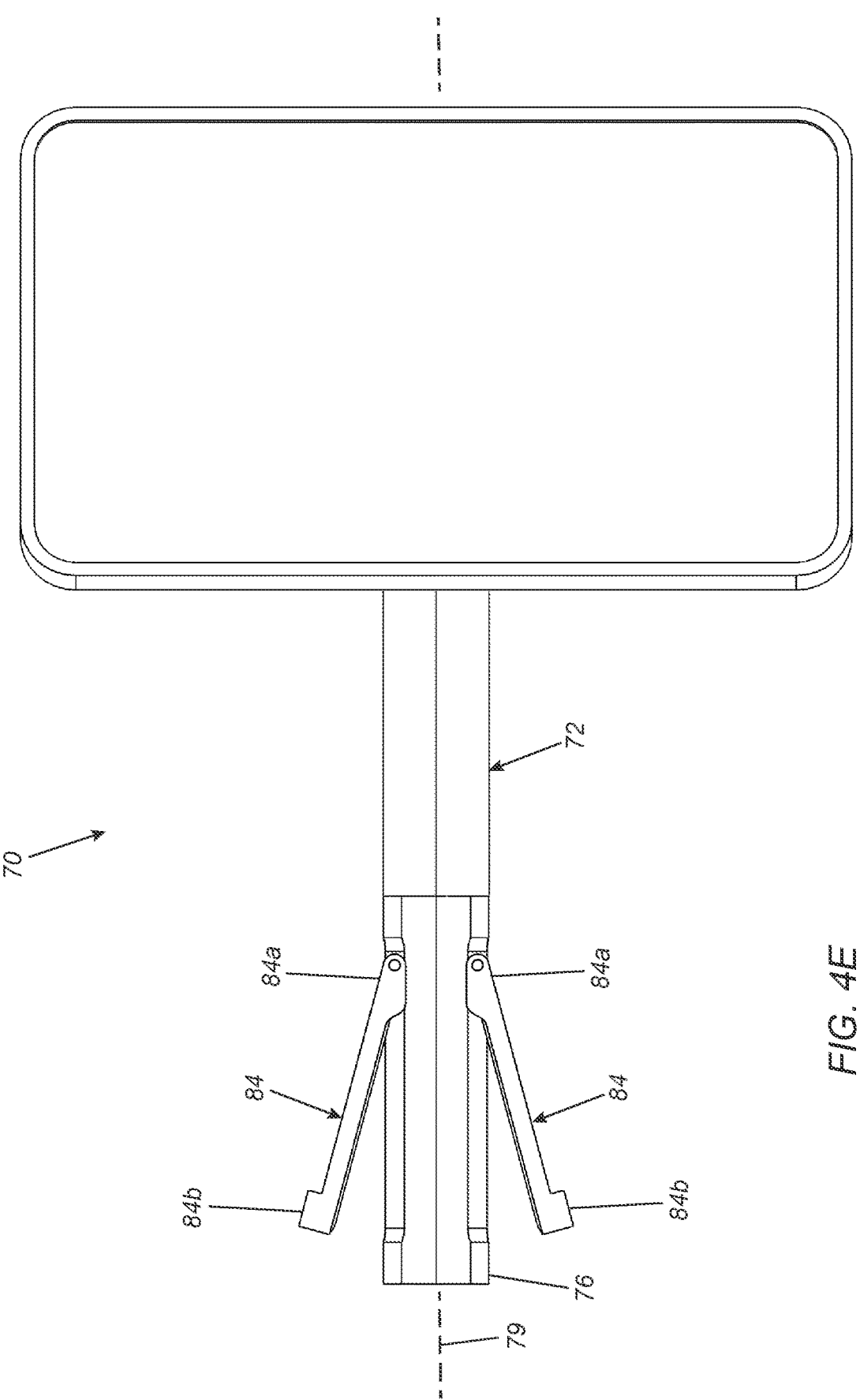
Figure 5A:
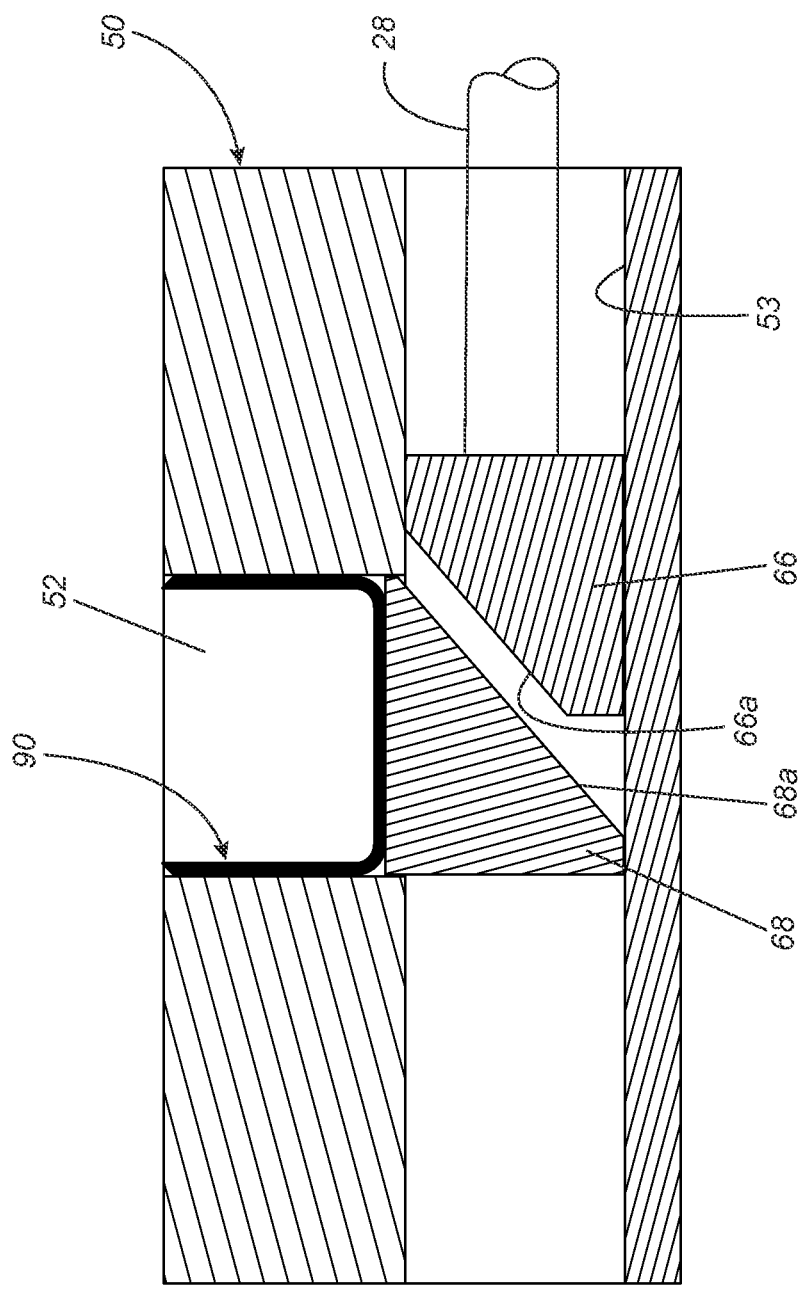
FIGS. 5A-5D are details showing a wedge actuation mechanism for deploying a staple from a cartridge received in a jaw of an end effector.
Figure 5B:
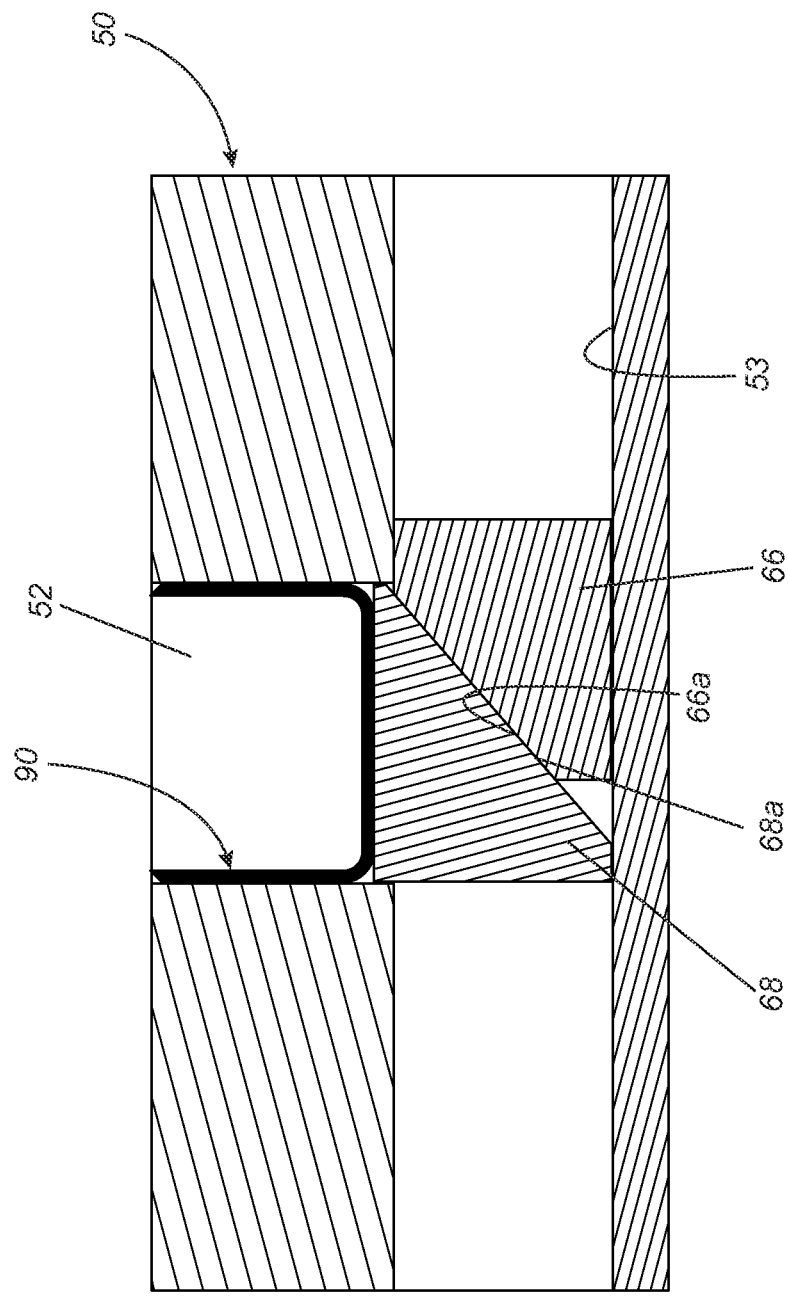
Figure 5C:
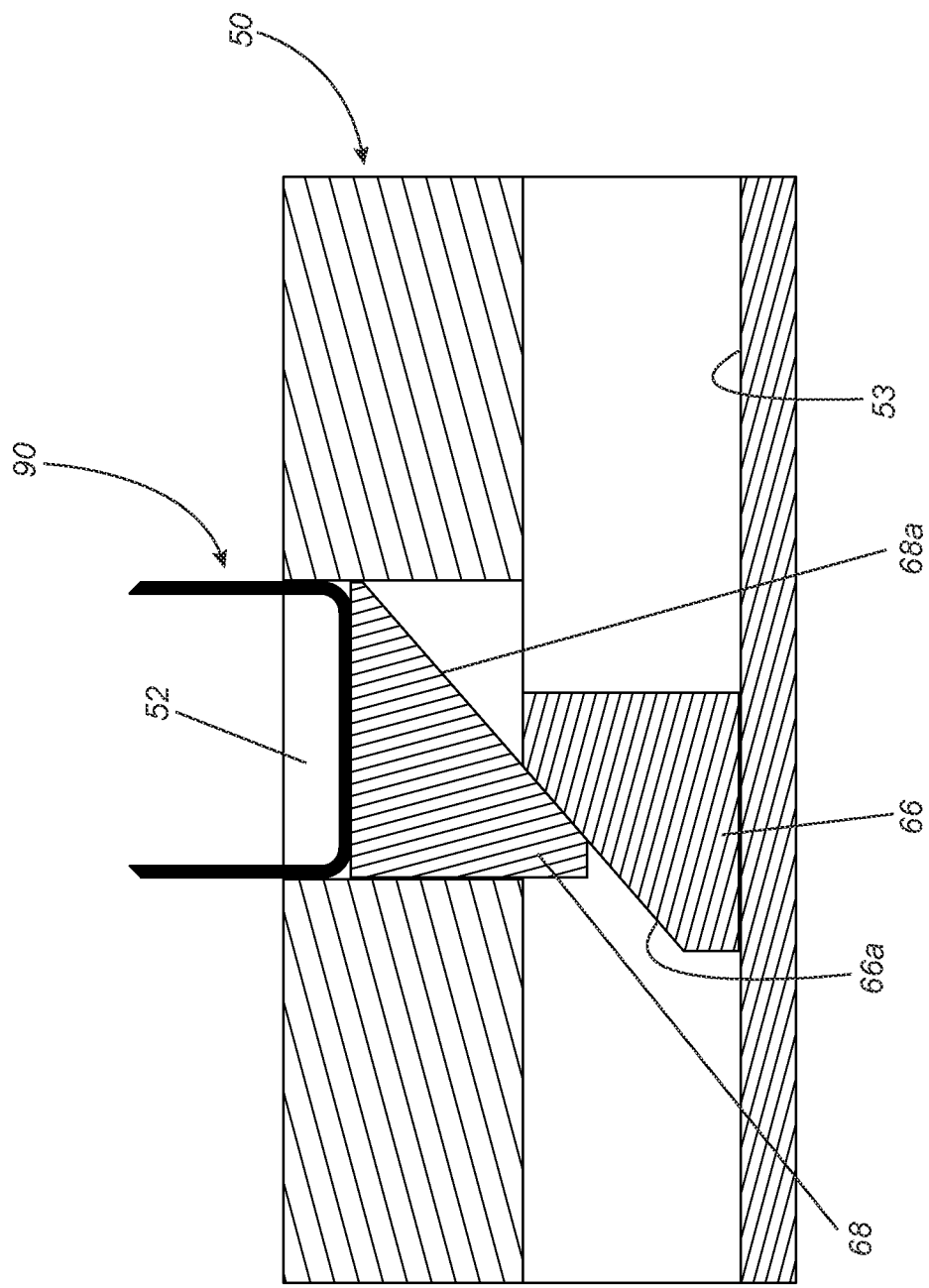
Figure 5D:
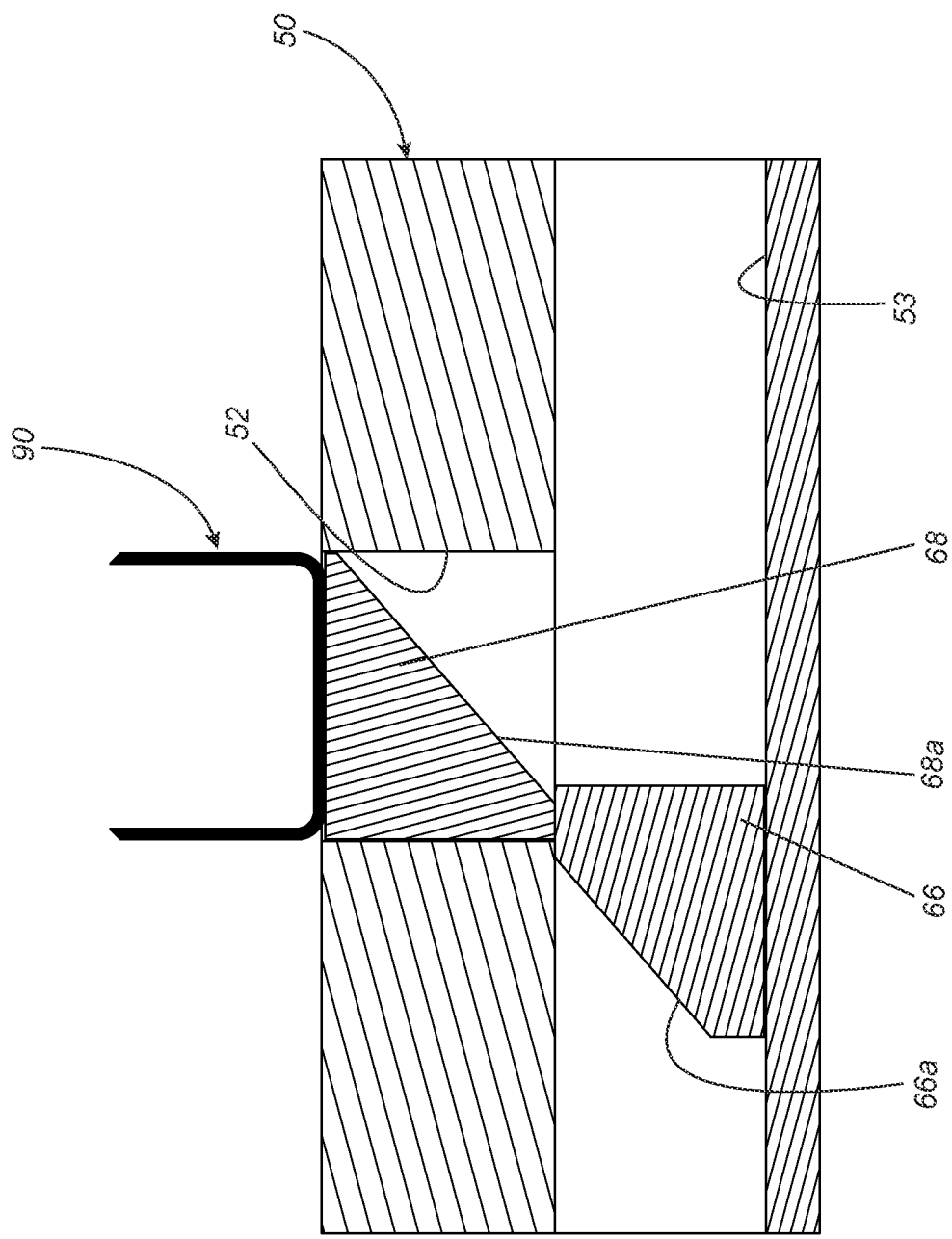

The arms 84 are movable between a retracted configuration, e.g., as shown in FIGS. 4A and 4D, which may facilitate introduction of the apparatus 8 into a patient's body, and a deployed configuration, e.g., as shown in FIGS. 4B, 4C, and 4E, where the imaging device may be used to acquire images during a procedure. In one example, the arms 84 may be actuated (or moved) by a user selectively between the retracted and deployed configurations, e.g., using an actuator (not shown) on the hub 80.

Returning to FIGS. 2A and 2B, the apparatus 8 may be used to deliver staples into tissue during a medical procedure, e.g., during a laparoscopic surgical procedure, such as an appendectomy. Initially, a surgical space may be created, e.g., by introducing a trocar and/or cannula device (not shown) through the patient's skin and intervening tissue to a target region, e.g., the patient's abdominal cavity, and insufflating or otherwise opening the space to access a desired tissue structure, such as an appendix indicated for removal.

An end effector 40 and cartridge 50 may be selected and connected to the distal end 24 of the shaft 20 before introduction into the patient's body. For example, based on the anatomy encountered, the operator may select a cartridge 50 including a particular arrangement of staples, e.g., including uniform-size staples or different size staples, such as those described elsewhere herein, insert the cartridge 50 into the cavity 46c of the first jaw 46, e.g., before or after connecting the end effector 40 the shaft 20. Once the apparatus 8 is ready, the distal end 24 of the shaft 20 carrying the end effector 40 may be introduced into the surgical space, e.g., through a cannula or other port (not shown), until the jaws 46, 48 are located within the surgical space. For example, the surgical space may be initially accessed using a needle, trocar, and/or dilator device, e.g., punctured through the patient's skin and intervening tissue into the abdominal cavity to approach the appendix, and a cannula may be positioned through the puncture. Gas may be delivered through the cannula or other device to insufflate and create a surgical cavity or space.

The distal end 24 of the shaft 40, carrying the selected end effector 40 and/or cartridge 50, may then be introduced through the cannula into the surgical space. For example, the jaws 46, 48 may be initially locked in the closed position to facilitate introduction through the cannula and then may be released once located within the surgical space, whereupon the second jaw 48 may open. Alternatively, the second jaw 48 may be biased to open but may be manually or otherwise closed to allow insertion through the cannula.

With the jaws 46, 48 in the open position within the surgical space, tissue within the region, e.g., the patient's appendix, may be placed on the contact surface 46a of the first jaw 46 and/or otherwise positioned between the jaws 46, 48. The target tissues within the surgical space may be exposed and/or otherwise presented using conventional instruments and methods before using the apparatus 8. For example, during an appendectomy procedure, both the appendix and the appendicular artery may be exposed and positioned between the jaws 46, 48, e.g., with one distal to the other depending on the orientation of the appendix.

Once the tissue is positioned as desired, the first trigger actuator 34 may be manipulated to close the second jaw 48 and lock the tissue in place between the contact surfaces 46a, 48a. For example, the trigger 34 may include a ratchet mechanism that allows the second jaw 48 to close while preventing it from reopening, or a separate locking mechanism (not shown) may be activated once the second jaw 48 is closed to engage the tissue. The second staple actuator 36 may then be used to deploy one or more staples from the first jaw 46 into and through the tissue and towards the second jaw 48 to deform the staples(s) and engage the tissue.

For example, as shown in FIGS. 5A-5D, as the stapler actuator 36 is pushed, the actuation shaft 28 within the shaft 20 may advance the wedge 66 or other staple actuation element within the cartridge 50 or end effector 40 to begin deploying staples from the receptacles 52 out of the first contact surface 50a/46a of the first jaw 46 upwardly towards the second jaw 48, thereby causing one or more tines of the staples to contact the corresponding recesses 54 in the second contact surface 48a and deform to staple the tissue. FIGS. 5A-5D show an example of a wedge actuator 66 slidable within a passage 53 within a cartridge 50 that includes an angled or ramped distal surface 66a that may push corresponding ramped surfaces 68a of pistons (one piston 68 shown) within respective receptacles 52 upwardly to push the corresponding staples 90 towards the second jaw 48 (not shown in FIGS. 5A5D), where tines of the staples 90 are deformed within the corresponding recesses 54, as described elsewhere herein. For example, the wedge 66 may be coupled to the stapler actuator shaft 28 that may be advanced and retracted within the passage 53, e.g., to advance the wedge 66, thereby slidably engaging the ramped surface 66a of the wedge 66 with ramped surfaces 68a of the pistons 68 and directing the pistons 68 upwardly in the respective receptacles 52, as shown in FIGS. 5A-5D.

Figure 6A:
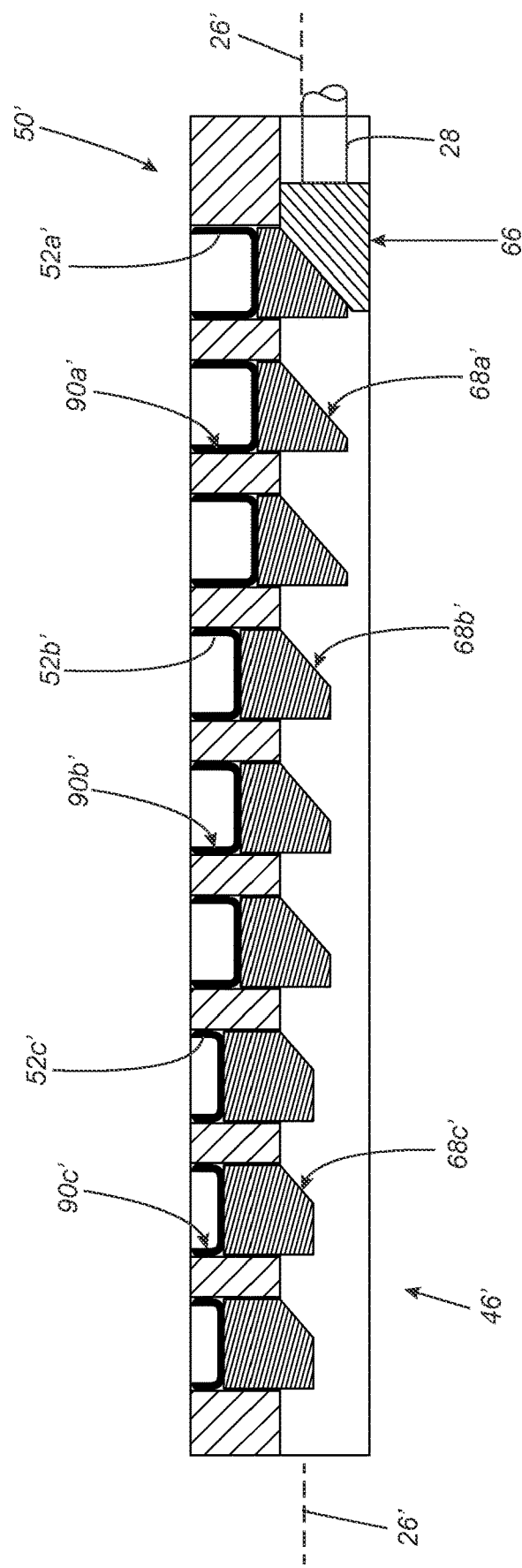
Figure 6B:
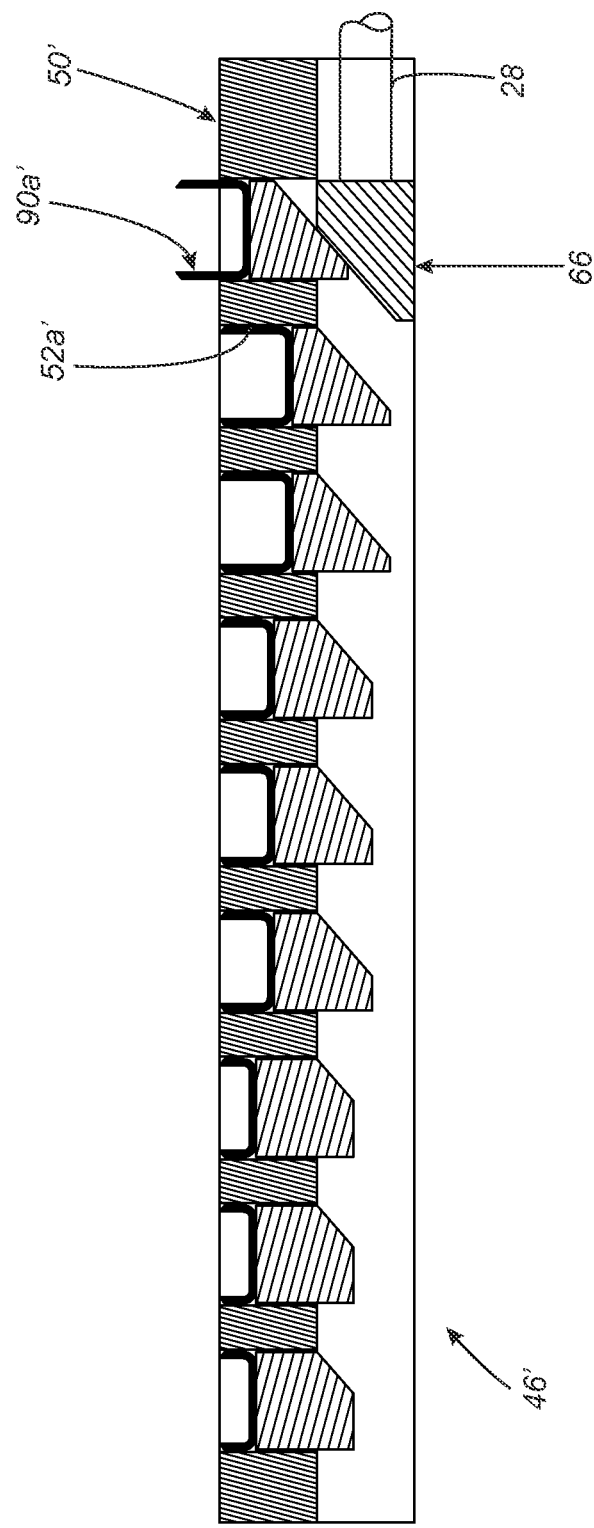
Figure 6C:
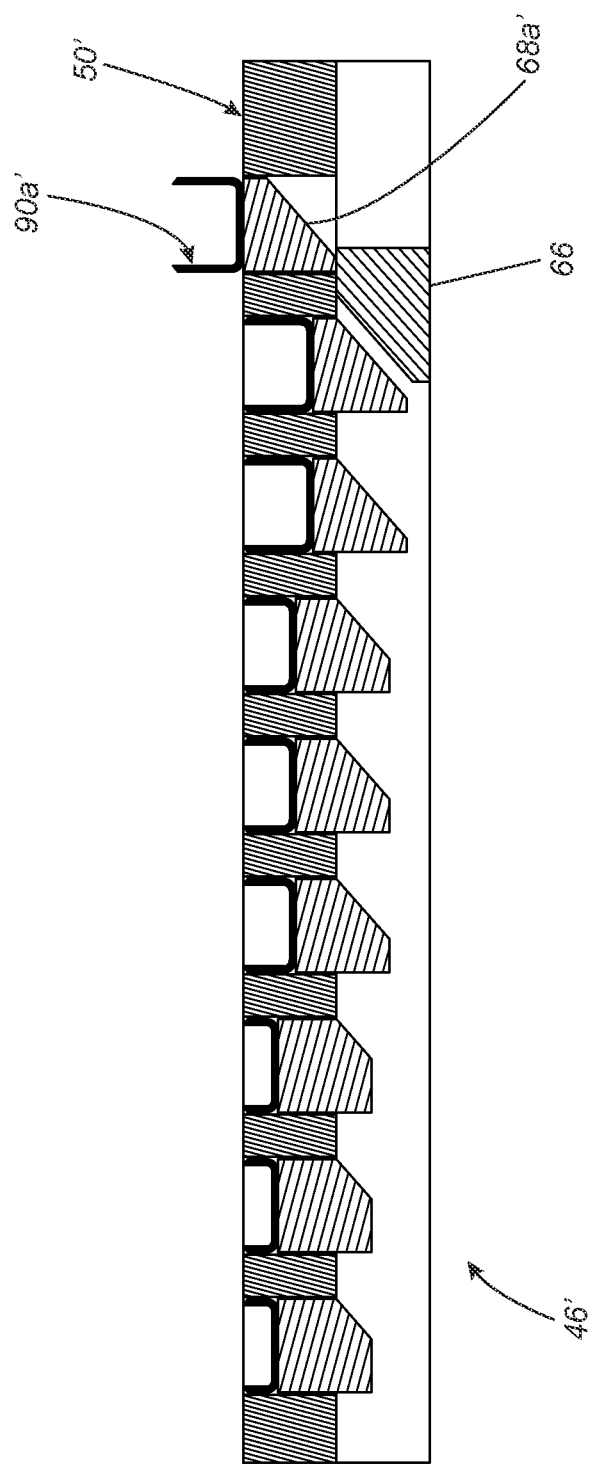
Figure 6D:
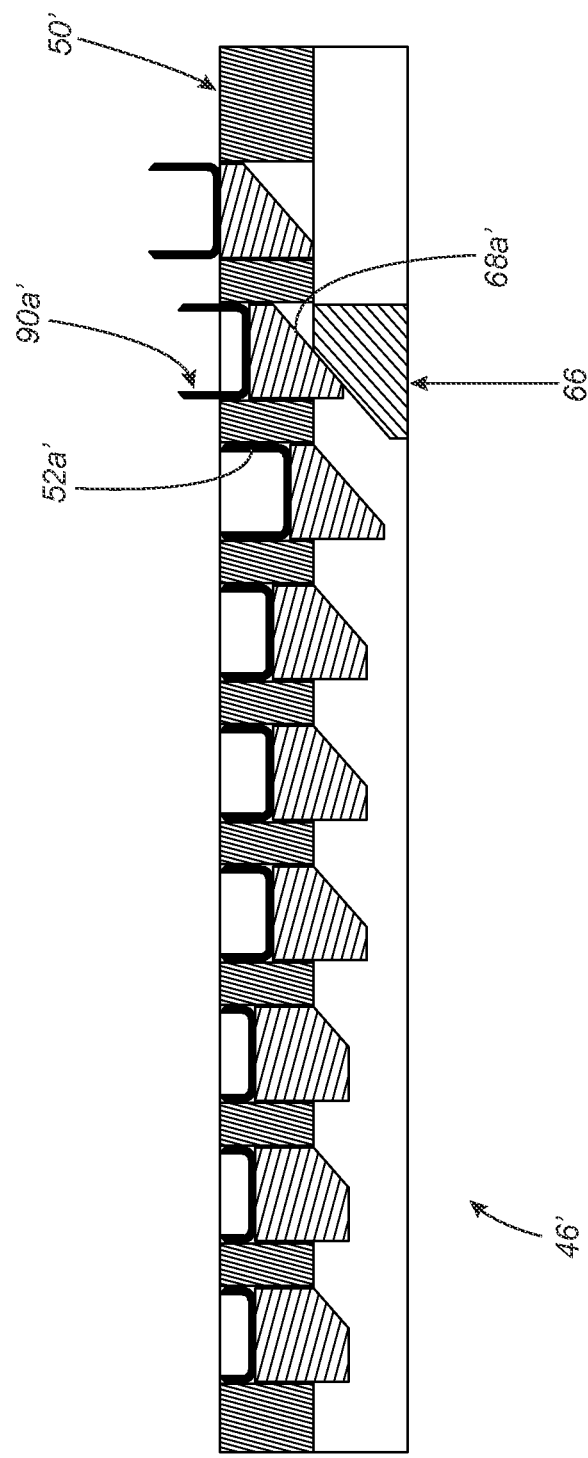
Figure 6E:
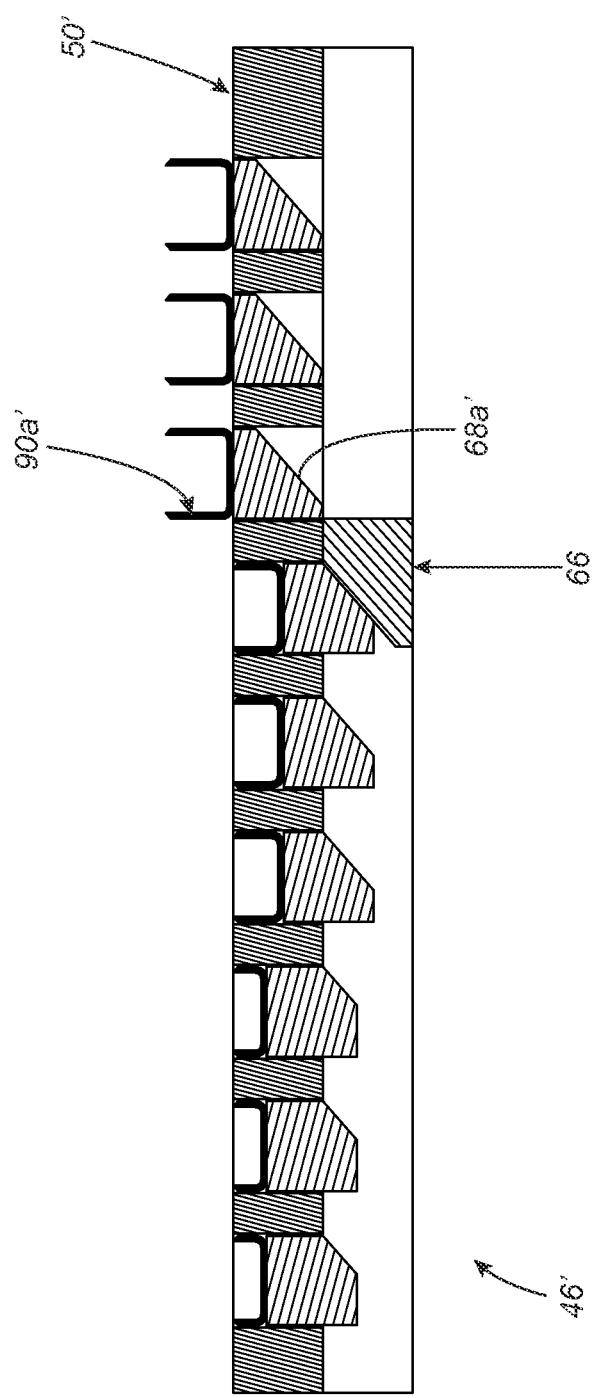
Figure 6F:
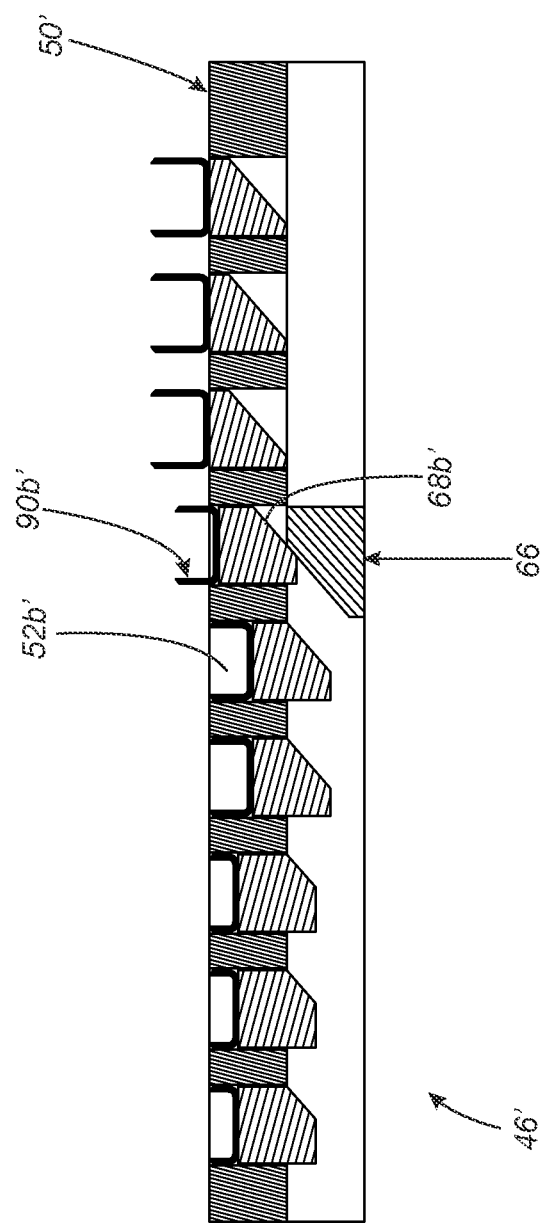
Figure 6G:
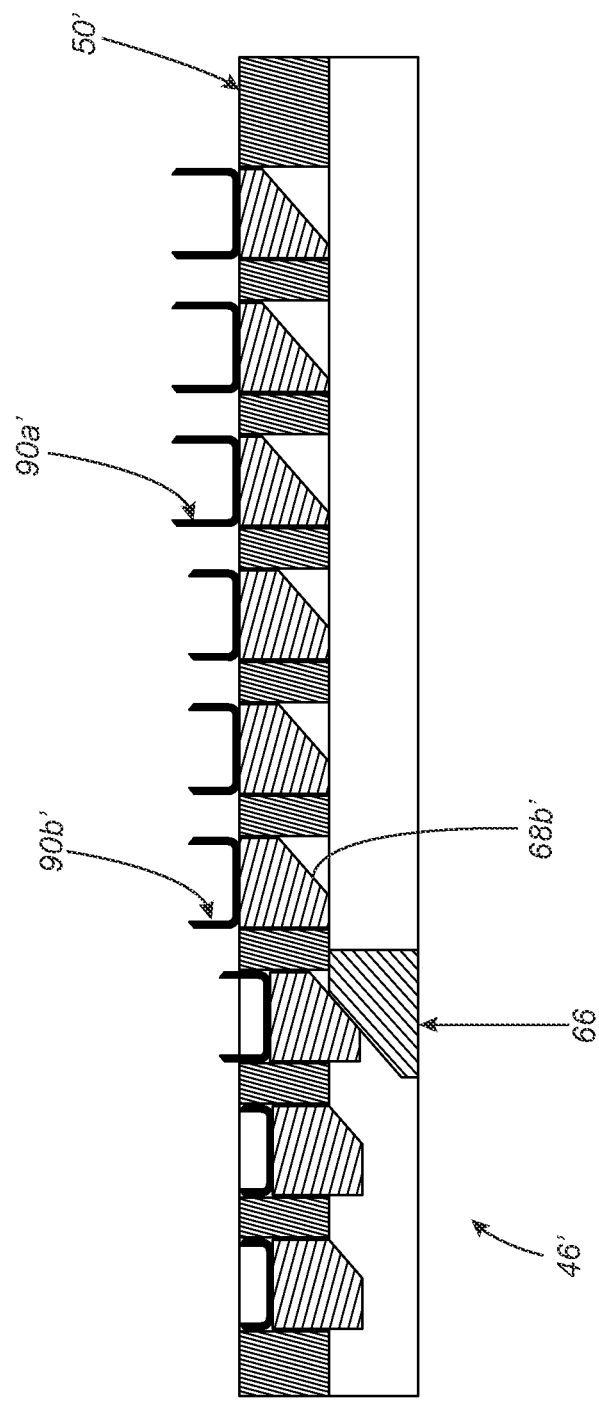
Figure 6H:
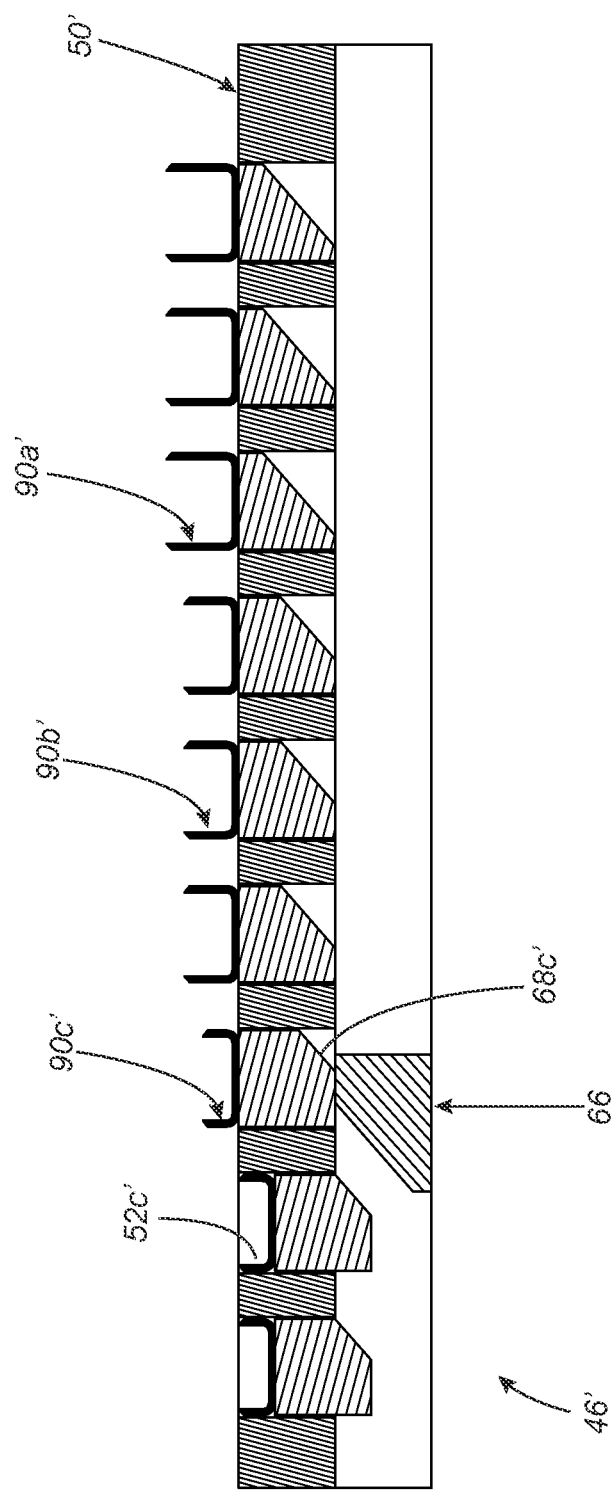
Figure 6I:
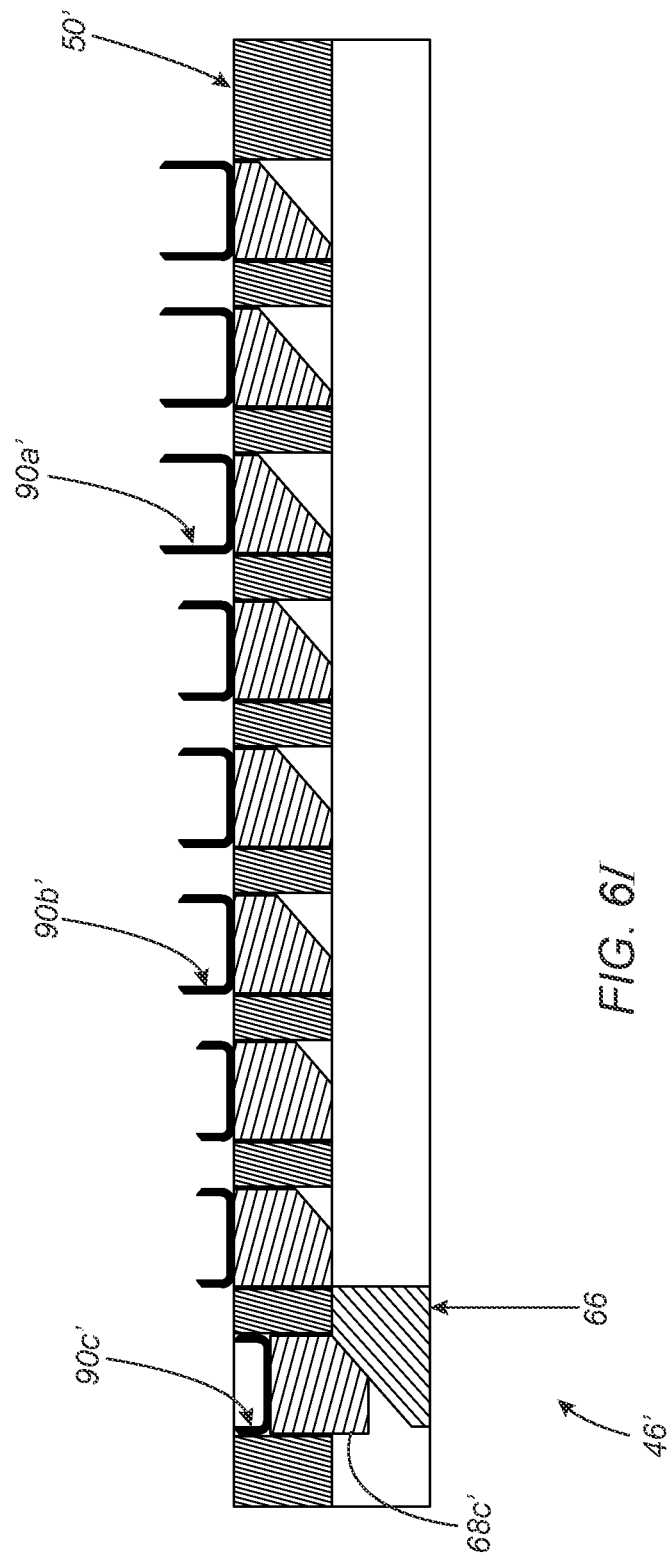

FIGS. 6A-6J show an alternative arrangement of receptacles 52' and staples 90' within a cartridge 50' that includes different sizes of receptacles 52' and staples 90'. As can be seen, as the shaft 28 and wedge 66 are advanced distally, the ramped surface 66a of the wedge 66 may engage the pistons 68' sequentially, thereby directing the pistons 68' upwardly to deploy the respective staples 90'. Thus, in a single continuous motion, the larger proximal staples 90a' may be deployed first, as shown in FIG. 6E, followed by the central staples 90b' as shown in FIG. 6G, and finally the distal staples 90c', as shown in FIG. 6J.

Alternatively, it will be appreciated that other stapler mechanisms may be provided in the apparatus 8, such as those disclosed in U.S. Pat. Nos. 4,608,981, 4,633,874, 5,104,025, 5,307,976, 5,709,680, and European Patent No. 1,157,666, the entire disclosures of which are expressly incorporated by reference herein.

With additional reference to FIG. 3A, the deployment of the staples may be sequential within each set or row, e.g., simultaneously delivering first staples from each of the rows 52a-52c at the proximal end of the first jaw 46 and, as the trigger 34 continues to be pulled, additional staples are deployed until the desired length of stapling, whereupon actuation may be discontinued, which may leave one or more staples closest to the distal tip 46a of the first jaw 46 undeployed. In this manner, the operator may control how many staples are deployed based on the extent to which the staple actuator is pulled. Alternatively, the actuator 34 may be binary, i.e., wherein, when the trigger 34 is initially pulled, all of the staples in the first jaw 46 are deployed in rapid succession.

Upon deploying all (or the desired number of staples), the apparatus 8 may then be removed from the surgical space and the procedure completed using conventional methods. For example, after deploying the staples 90, the end effector 40 may be removed from the patient's body with the second jaw 48 remaining locked to remove the excised tissue. Optionally, the wedge 66 may be retracted back to the position shown in FIG. 5A or 6A before removing the apparatus 8 or the wedge 66 may remain in its distal-most position.

The procedure may be illuminated and/or monitored using the imaging elements on the imaging sleeve 70. Optionally, during the procedure, the imaging sleeve 70 may be advanced and/or retracted relative to the shaft 20, as desired, to adjust the field of view and/or otherwise facilitate visualization during the procedure.

It will be appreciated that elements or components shown with any example herein are exemplary for the specific example and may be used on or in combination with other examples disclosed herein. In addition, although the apparatus herein have been described for particular use during an appendectomy procedure. It will be appreciated that the apparatus and methods herein may be used in a variety of surgical procedures, e.g., including open, minimally invasive, laparoscopic, and other procedures, where it is desired to staple and remove target tissues, e.g., within a patient's intestine, lungs, vasculature, and other locations.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for performing a medical procedure, comprising:
   a shaft comprising a proximal end, a distal end sized for introduction into a patient's body, and a longitudinal axis extending between the proximal and distal ends;
   first and second jaws on the distal end of the shaft that are movable relative to one another between open and closed positions, thereby directing first and second contact surfaces of the first and second jaws away from and towards one another, respectively;
   first and second sets of staples carried by the first jaw and positioned in rows parallel to the longitudinal axis, wherein at least some of the staples are a different size than other staples; and
   a handle on the proximal end of the shaft comprising:
      a first actuator for directing one or both of the first and second jaws to the closed position to secure tissue between the first and second contact surfaces,
      a second actuator for deploying the staples from the first jaw through the secured tissue towards the second jaw to deform the staples; and
   an imaging assembly carried on the shaft comprising:
      an elongate tubular member mounted over the shaft comprising a proximal portion positioned adjacent the handle, and a distal portion positioned adjacent the first and second jaws;
      a pair of deployment arms on the distal portion, each deployment arm comprising a first end pivotably coupled to the tubular member and a second free end that is movable from a retracted position wherein the second end is aligned against or within a wall of the tubular member to allow the distal portion to be introduced into the patient's body when the distal end of the shaft is introduced into the patient's body to a deployed position wherein the second end moves outwardly relative to the longitudinal axis; and
      an imaging element on the second end of each deployment arm proximal to the first and second jaws to provide images from within the patient's body,
      wherein the tubular member is movable axially relative to the shaft to adjust a field of view of the imaging element on each deployment arm.

2. The apparatus of claim 1, further comprising:
   a cartridge carried by the first jaw carrying the first and second sets of staples; and
   a display on the proximal end coupled to the imaging element on each deployment arm for displaying images beyond the distal end.

3. The apparatus of claim 2, wherein the first and second jaws are carried on an end effector removable from the distal end of the shaft.

4. The apparatus of claim 2, wherein the cartridge is removable from the first jaw.

5. The apparatus of claim 2, wherein the cartridge at least partially defines the first contact surface.

6. The apparatus of claim 2, wherein all of the staples in the first set are a different size than all of the staples in the second set.

7. The apparatus of claim 2, wherein the first set or the second set of staples comprises a first subset of staples and a second subset of staples, and wherein the second subset of staples are a different size than the first subset of staples.

8. The apparatus of claim 2, wherein the first jaw is fixed relative to the shaft and the second jaw is pivotable relative to the first jaw between the open position to allow tissue to be positioned on the contact surface, and the closed position to secure the tissue between the first and second contact surfaces.

9. The apparatus of claim 8, wherein the first actuator comprises a trigger for directing the second jaw from the open position to the closed position to secure the tissue between the first and second contact surfaces and the second actuator is actuatable independent of the trigger for driving the one or more staples from the first jaw through the tissue and towards the second jaw to staple the tissue.

10. The apparatus of claim 2, wherein the display is mounted on a proximal portion of the tubular member.

11. The apparatus of claim 1, wherein the deployment arms comprise first and second arms, the first arm carrying an illumination source on the second end thereof, and the second arm carrying a camera on the second end thereof.

12. The apparatus of claim 11, wherein the imaging element comprises a lens carried on the second end of the second arm and wherein a fiber optic element extends from the lens to the camera for delivering images to the camera.

13. The apparatus of claim 12, wherein the camera is coupled to a processor located within a housing carrying the display, the processor configured to process the signals from the camera for presentation on the display.

14. The apparatus of claim 1, further comprising an actuator on the proximal end of the tubular member for selectively directing the deployment arms between the retracted and deployed positions.

15. The apparatus of claim 1, wherein the deployment arms are mounted on the tubular member on opposite sides of the distal portion.

16. The apparatus of claim 1, wherein the imaging element comprises a camera on the second end of each deployment arm.

17. The apparatus of claim 16, further comprising one or more light sources on the second end of each deployment arm.

18. The apparatus of claim 16, wherein the apparatus is configured to acquire images from camera on each deployment arm simultaneously.

19. The apparatus of claim 1, wherein the shaft and the tubular member are both substantially rigid such that the end effector is aligned with the longitudinal axis.

20. An apparatus for performing a medical procedure, comprising:
a substantially rigid shaft comprising a proximal end, a distal end sized for introduction into a patient's body, and a longitudinal axis extending between the proximal and distal ends;
first and second jaws on the distal end of the shaft that are movable relative to one another between open and closed positions, thereby directing first and second contact surfaces of the first and second jaws away from and towards one another, respectively;
an end effector carried by the first jaw carrying first and second sets of staples positioned in rows parallel to the longitudinal axis, wherein at least some of the staples are a different size than other staples; and
a handle on the proximal end of the shaft comprising:
a first actuator for directing one or both of the first and second jaws to the closed position to secure tissue between the first and second contact surfaces, and
a second actuator for deploying the staples from the first jaw through the secured tissue towards the second jaw to deform the staples;
an elongate tubular member carried on the shaft comprising a proximal portion positioned adjacent the handle, a distal portion positioned adjacent the end effector;
a pair of deployment arms on the distal portion proximal to the end effector comprising first ends pivotably coupled to the tubular member and second free ends that are movable from a retracted position wherein the second ends are aligned against or within a wall of the tubular member for introduction into the patient's body when the distal end of the shaft is introduced into the patient's body to a deployed position wherein the second ends move outwardly relative to the longitudinal axis;
cameras on the second ends of the deployment arms to provide images from within the patient's body; and
a display on the proximal end coupled to the cameras for displaying the images,
wherein the tubular member is movable axially relative to the shaft to adjust a field of view of the cameras.

21. The apparatus of claim 20, wherein, in the deployed position, the cameras include a field of view oriented distally beyond the distal portion to illuminate and image the end effector deployed within a region beyond the distal portion.

22. The apparatus of claim 20, wherein the deployment arms are mounted on the tubular member on opposite sides of the distal portion.

23. The apparatus of claim 20, further comprising one or more light sources on the second ends of the deployment arms.

24. The apparatus of claim 20, wherein the cameras are configured to acquire images simultaneously.

25. An apparatus for performing a medical procedure, comprising:
a substantially rigid shaft comprising a proximal end, a distal end sized for introduction into a patient's body, and a longitudinal axis extending between the proximal and distal ends;
first and second jaws on the distal end of the shaft that are movable relative to one another between open and closed positions, thereby directing first and second contact surfaces of the first and second jaws away from and towards one another, respectively;
an end effector carried by the first jaw carrying first and second sets of staples positioned in rows parallel to the longitudinal axis, wherein at least some of the staples are a different size than other staples;
a handle on the proximal end of the shaft comprising:
a first actuator for directing one or both of the first and second jaws to the closed position to secure tissue between the first and second contact surfaces, and
a second actuator for deploying the staples from the first jaw through the secured tissue towards the second jaw to deform the staples;
an imaging assembly carried on the shaft comprising a proximal portion positioned adjacent the handle, a distal portion positioned adjacent the end effector, one or more imaging elements on one or more deployment arms on the distal portion proximal to the end effector configured for introduction into the patient's body when the distal end of the shaft is introduced into the patient's body to provide images from within the patient's body, and a display on the proximal end coupled to the one or more imaging elements for displaying images beyond the distal end; and
an elongate tubular member mounted over the shaft comprising the proximal and distal portions,
wherein each of the one or more deployment arms comprises a first end pivotably coupled to the tubular member and a second free end that is movable from a retracted position wherein the second end is aligned against or within a wall of the tubular member to allow the distal portion to be introduced into the patient's body when the distal end of the shaft is introduced into the patient's body to a deployed position wherein the second end moves outwardly relative to the longitudinal axis for presenting images on the display when the distal portion is within the patient's body, and
wherein the tubular member is movable axially relative to the shaft to adjust a field of view of the one or more imaging elements.

* * * * *